US012422396B2

(12) United States Patent
Dhamu et al.

(10) Patent No.: US 12,422,396 B2
(45) Date of Patent: Sep. 23, 2025

(54) SYSTEMS AND METHODS FOR MULTI-MODAL AND MULTIPLEXED ELECTROCHEMICAL DETECTION AND REPORTING OF ENVIRONMENTAL CONTAMINANTS

(71) Applicant: EnLiSense LLC, Allen, TX (US)

(72) Inventors: Vikram Narayanan Dhamu, Dallas, TX (US); Sriram Muthukumar, Allen, TX (US)

(73) Assignee: EnLiSense LLC, Allen, TX (US)

( * ) Notice: Subject to any disclaimer, the term of this patent is extended or adjusted under 35 U.S.C. 154(b) by 313 days.

(21) Appl. No.: 18/323,933

(22) Filed: May 25, 2023

(65) Prior Publication Data

US 2024/0393287 A1 Nov. 28, 2024

(51) Int. Cl.
*G01N 27/327* (2006.01)
*G01N 27/02* (2006.01)
(Continued)

(52) U.S. Cl.
CPC ....... *G01N 27/3277* (2013.01); *G01N 27/021* (2013.01); *G01N 33/1826* (2013.01);
(Continued)

(58) Field of Classification Search
CPC ........... G01N 27/3277; G01N 33/1826; G01N 33/184; G01N 33/025; G01N 33/04;
(Continued)

(56) References Cited

U.S. PATENT DOCUMENTS 4,225,410 A * 9/1980 Pace .................... G01N 33/492
    435/817
5,217,594 A * 6/1993 Henkens ................ C12Q 1/005
    435/817
(Continued)

FOREIGN PATENT DOCUMENTS

CN     101875968 A    11/2010
CN     102094086 B    10/2012
(Continued)

OTHER PUBLICATIONS

Jacobs, *Ultra-Senstive Electrical Immunoassay Biosensors Using Nanotextrured Zinc Oxide Thin Films on Printed Circuit Board Platforms*, Biosensors and Bioelectronics, 55, 2014, pp. 7-13.
(Continued)

*Primary Examiner* — Alexander S Noguerola
(74) *Attorney, Agent, or Firm* — Aambell PC

(57) ABSTRACT

Embodiments of an apparatus are disclosed, the apparatus comprising: a substrate having a first end and an opposite, second end; a plurality of sensors proximate to the first end of the substrate, each sensor including: a first electrode; a second electrode at least partially surrounding the first electrode; and an active sensing element over the first electrode, a surface of the active sensing element being functionalized detect analytes in a sample derived from an environmental source; a plurality of contact pads proximate to the second end of the substrate, each contact pad being conductively coupled to the first electrode or the second electrode of a corresponding sensor in the plurality of sensors; and a cartridge surrounding the plurality of sensors and providing an enclosed space to contain the sample over the plurality of sensors.

20 Claims, 12 Drawing Sheets

(51) Int. Cl.
*G01N 33/18* (2006.01)
*G01N 33/02* (2006.01)
*G01N 33/04* (2006.01)
*G01N 33/12* (2006.01)
*G01N 33/44* (2006.01)

(52) U.S. Cl.
CPC ........... *G01N 33/025* (2013.01); *G01N 33/04* (2013.01); *G01N 33/12* (2013.01); *G01N 33/184* (2024.05); *G01N 33/442* (2013.01)

(58) Field of Classification Search
CPC .. G01N 33/12; G01N 33/442; G01N 33/4836; G01N 27/02; G01N 27/021
See application file for complete search history.

(56) References Cited

U.S. PATENT DOCUMENTS

| | | | |
|---|---|---|---|
| 6,247,350 B1 * | 6/2001 | Tsukuda | B01L 3/5085 |
| | | | 73/19.1 |
| 8,623,196 B2 | 1/2014 | Kohli et al. | |
| 8,758,584 B2 | 6/2014 | Kahn et al. | |
| 9,064,965 B2 | 6/2015 | Lu et al. | |
| 9,846,136 B2 | 12/2017 | Wu et al. | |
| 10,006,882 B2 | 6/2018 | Prasad et al. | |
| 10,107,770 B2 | 10/2018 | Weindorf et al. | |
| 10,954,144 B2 | 3/2021 | Ball et al. | |
| 2002/0197390 A1 | 12/2002 | Lewis et al. | |
| 2005/0029445 A1 | 2/2005 | Lee et al. | |
| 2009/0242399 A1 | 10/2009 | Kamath et al. | |
| 2011/0172559 A1 | 7/2011 | Fei et al. | |
| 2012/0125789 A1 | 5/2012 | Ocvirk et al. | |
| 2012/0261258 A1 * | 10/2012 | Macfie | G01N 27/3272 |
| | | | 204/403.14 |
| 2014/0011691 A1 | 1/2014 | Sierks et al. | |
| 2015/0011421 A1 | 1/2015 | Li et al. | |
| 2016/0146754 A1 | 5/2016 | Prasad et al. | |
| 2016/0291001 A1 | 10/2016 | Revzin et al. | |
| 2018/0263539 A1 | 9/2018 | Javey et al. | |
| 2019/0069818 A1 | 3/2019 | Prasad et al. | |
| 2019/0250153 A1 | 8/2019 | Muthukumar et al. | |
| 2019/0257829 A1 | 8/2019 | Ludwig et al. | |
| 2020/0054259 A1 | 2/2020 | Sankhala et al. | |
| 2021/0325380 A1 | 10/2021 | Muthukumar | |
| 2022/0120705 A1 * | 4/2022 | Mintchev | G01N 27/283 |
| 2022/0160265 A1 | 5/2022 | Sankhala et al. | |

FOREIGN PATENT DOCUMENTS

| | | | | |
|---|---|---|---|---|
| CN | 103091284 A | 5/2013 | | |
| CN | 102723784 B | 8/2014 | | |
| CN | 103578268 B | 7/2015 | | |
| CN | 104569271 B | 3/2016 | | |
| CN | 103534577 B | 12/2016 | | |
| CN | 107576618 B | 4/2020 | | |
| CN | 107426958 B | 8/2020 | | |
| CN | 107767032 B | 8/2020 | | |
| CN | 111914814 A | 11/2020 | | |
| CN | 107338310 B | 12/2020 | | |
| WO | WO-9940218 A1 * | 8/1999 | | C12Q 1/00 |
| WO | 2006052891 A1 | 5/2006 | | |
| WO | WO-2007106936 A1 * | 9/2007 | | G01N 33/50 |
| WO | 2012050646 A3 | 4/2012 | | |
| WO | 2016157117 A1 | 10/2016 | | |
| WO | 2018075824 A1 | 4/2018 | | |
| WO | WO-2020104933 A1 * | 5/2020 | | G01N 33/543 |

OTHER PUBLICATIONS

Ji, CN103675075 Machine Translation, 2014.
Munje, *Flexible Nanoporous Tunable Electrical Double Layer Biosensors for Sweat Diagnostics*, Scientific Reports, 2015, 5:14586, pp. 1-11.
PCT International Search Report and Written Opinion in PCT International Application Serial No. PCT/US2017/057478 mailed on Feb. 16, 2018, 17 pages.
Poudyal et al., *A Novel Single Step Method to Rapidly Screen for Metal Contaminants in Beverages, a Case Study with Aluminum*, Environmental Technology & Innovation 28 (2022) 102691, 12 pages.
Dhamu et al., *ElectrochemSENSE: A Platform Towards Field Deployable Direct On-Produce Glyphosate Detection*, Biosensors and Bioelectronics 170 (2020) 112609, 8 pages.
Stevenson et al., *Ultrasensitive and Rapid-Response Sensor for the Electrochemical Detection of Antibiotic Residues within Meat Samples*, ACS Publications, © 2019 American Chemical Society, 7 pages.
Sardesai et al., *Design and Electrochemical Characterization of Spiral Electrochemical Notification Coupled Electrode (SENCE) Platform for Biosensing Application*, Micromachines, 2020, 11, 333; doi: 10.3390/mi11030333, www.mdpi.com/journal/micromachines, 14 pages.
Paul et al., *Review—Room-Temperature Ionic Liquids for Electrochemical Application with Special Focus on Gas Sensors*, Journal of the Electrochemical Society, 2020 167 037511, 8 pages.
CN102094086b, English Translation of Abstract, 1 page, Oct. 17, 2012.
CN111914814A, English Translation of Abstract, 1 page, Nov. 10, 2020.
CN103091284A, English Translation of Abstract, 1 page, May 8, 2013.
CN107338310B, English Translation of Abstract, 1 page, Dec. 25, 2020.
CN107426958B, English Translation of Abstract, 1 page, Aug. 25, 2020.
CN107576618B, English Translation of Abstract, 1 page, Apr. 28, 2020.
CN101875968A, English Translation of Abstract, 1 page, Nov. 3, 2010.
CN102723784B, English Translation of Abstract, 1 page, Aug. 20, 2014.
CN104569271B, English Translation of Abstract, 1 page, Mar. 9, 2016.
CN103534577B, English Translation of Abstract, 1 page, Feb. 22, 2014.
CN107767032B, English Translation of Abstract, 1 page, Aug. 11, 2020.
CN103578268B, English Translation of Abstract, 1 page, Jul. 15, 2015.

* cited by examiner

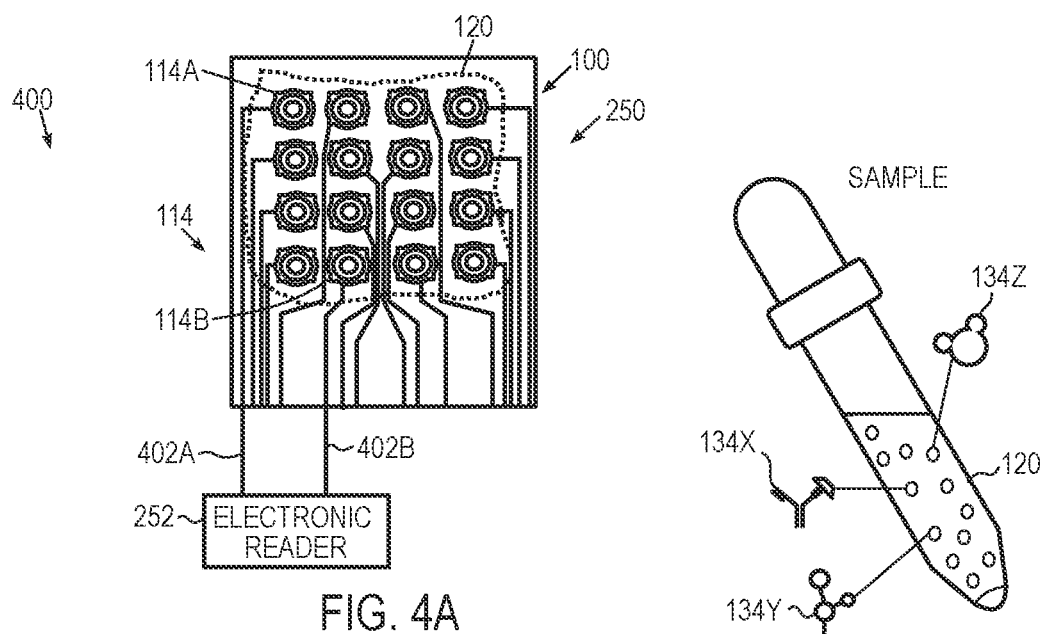
FIG. 4A
FIG. 4B
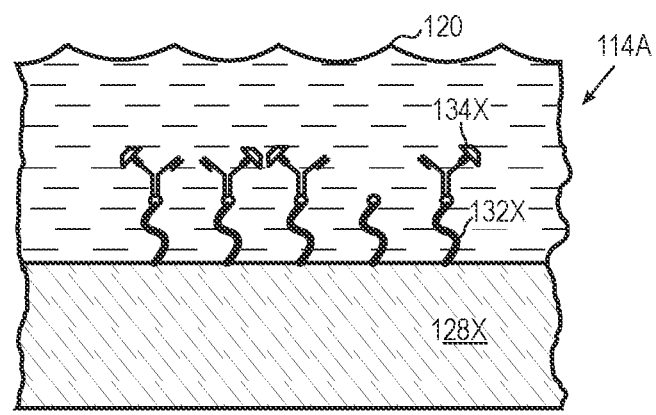
FIG. 4C
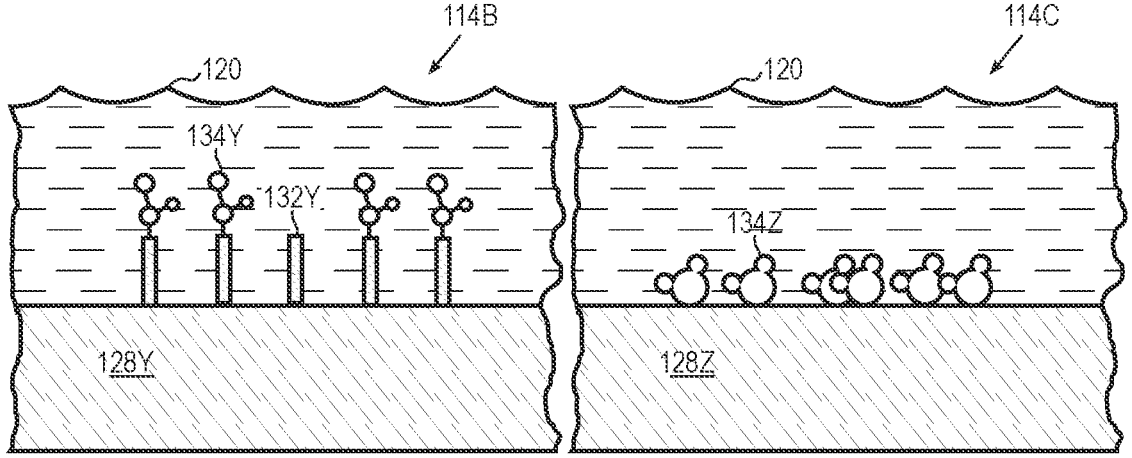
FIG. 4D
FIG. 4E

SYSTEMS AND METHODS FOR MULTI-MODAL AND MULTIPLEXED ELECTROCHEMICAL DETECTION AND REPORTING OF ENVIRONMENTAL CONTAMINANTS

TECHNICAL FIELD

The present disclosure relates to systems, techniques, and methods directed to multi-modal and multiplexed electrochemical detection and reporting of environmental contaminants.

BACKGROUND

In general, environmental contaminants include any physical, chemical, or biological substance that has an adverse effect on air, water, soil, or living organisms. A wide range of such environmental contaminants find their way into food chains, water cycles, and everyday goods. For example, some chemicals resist breakdown and accumulate in the food chain; these chemicals are then absorbed by plants, or consumed by fish and wildlife, which in turn may be eaten by humans, negatively impacting human health. Further, there is significant risk to people, in terms of both short-term illnesses and long-term chronic health problems, in consuming food or water that is polluted with pathogens or chemical pollutants. In yet another example, food, drinks, supplements, and beauty products derived from crops and animal products may be contaminated with toxic pesticides that have long-term detrimental impact on human and environmental health. Hence, there is a need to detect and monitor such environmental contaminants quickly and efficiently as a first step towards preventing exposure.

BRIEF DESCRIPTION OF DRAWINGS

Embodiments will be readily understood by the following detailed description in conjunction with the accompanying drawings. To facilitate this description, like reference numerals designate like elements. Embodiments are illustrated by way of example, and not by way of limitation, in the figures of the accompanying drawings.

FIGS. 4A-4E are simplified block diagrams illustrating example details of a system for multi-modal and multiplexed electrochemical detection and reporting of environmental contaminants, according to some embodiments of the present disclosure.

DETAILED DESCRIPTION

Overview

Figure 1A:
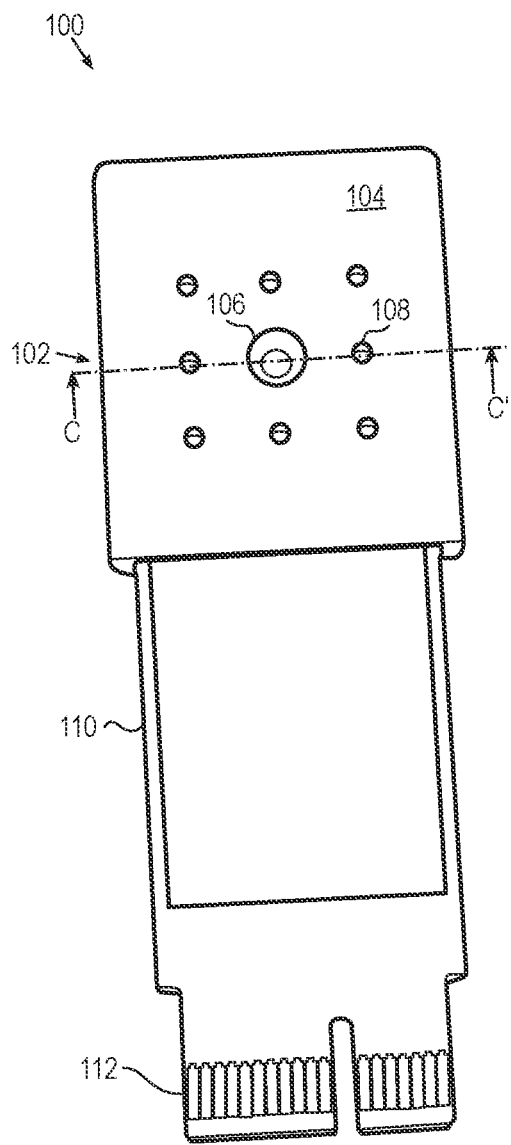
FIGS. 1A-1F are simplified block diagrams illustrating example details of a electrode strip used in a system for multi-modal and multiplexed electrochemical detection and reporting of environmental contaminants, according to some embodiments of the present disclosure.

For purposes of illustrating the embodiments described herein, it is important to understand certain terminology and operations of sensing systems. The following foundational information may be viewed as a basis from which the present disclosure may be properly explained. Such information is offered for purposes of explanation only and, accordingly, should not be construed in any way to limit the broad scope of the present disclosure and its potential applications.

Environmental contaminants are associated with health risks in humans, including cancer and disorders of the nervous, endocrine, and reproductive systems. They are diverse, ranging from chemical, to physical, biological, and radiological compounds, and are widely spread in air, soil, and water. Some toxins are so lethal that trace detection of their presence in food, water, soil, and other objects is critical to prevent exposure. For example, the Centers for Disease Control reports that 48 million people—or one out of every six Americans are prone to food borne illnesses per annum, of whom, 128,000 are hospitalized and 3,000 die from the illnesses. Examples of these pathogens include *Salmonella, E. Coli* O157*, Campylobacter, Listeria*, Hepatitis A, Norovirus, Poliovirus, Rotavirus, Coxsackievirus, and Coliforms. Among these, *Salmonella* alone contributes to more than 1 million cases in the United States. Yet, in many instances, it is not feasible, using current methods, to quickly and efficiently detect, isolate and decouple sources of these pathogens until an outbreak occurs, in part because contaminated food looks no different from uncontaminated food.

Current methods to detect pathogenic contamination in food or water include culture counting, molecular diagnostics, and enzyme-linked immunosorbent assay (ELISA)-like assays, all of which require reagents with limited shelf-life, cold storage requirement, trained users, multiple manual steps, and long wait times. Many of these detection systems typically use multiple pieces of equipment for pre-enrichment or concentration of the pathogens in samples, followed by multiple steps to isolate the pathogens from the samples. Such procedures increase testing time and ultimately extend the overall time to detect the pathogens. In addition, the cold storage requirements for many of the reagents used in these procedures, prevent, or severely limit their applicability on the field, in real-time, under ordinary room temperature conditions, making them infeasible for rapid and immediate detections.

Another type of toxin found in food is a fungal metabolite called mycotoxin. Mycotoxins are produced by parasitic filamentous fungi belonging to the Ascomycota fungi phylum. The major producers of mycotoxins are *Aspergillus*, *Fusarium*, and *Penicilliums*. The most commonly occurring mycotoxins are Aflatoxins, Ochratoxins, Fumonisins, Zearalenone, Trichothecenes, and Patulin. Correlated health effects with ingestion and consumption of mycotoxin-contaminated food include acute and chronic illnesses, such as liver cancer, immunological diseases, metabolism modulations, gangrene, convulsions, and respiratory problems, among others. Despite their toxicity, they are abundant in the food supply, being found at high levels in food crops such as cereals, soybeans, certain fruits and nuts, as also plant-derived food products, and animal feed crops or products leading to mycotoxin contamination of milk, eggs, and meat. Due to their persistent prevalence, testing is necessary at multiple stages in the food supply chain to detect and remove them. Yet, methods for their detection may be different from those used to detect *Salmonella* and other bacterial or viral pathogens, which means that additional equipment is necessary to screen for both mycotoxins and bacteria/viral pathogens in food.

Current methods to test mycotoxin-contaminated foods use chromatography with mass spectrometry methods, thin-layer chromatography coupled with ultraviolet, fluorescence or mass spectrometry detectors. These techniques rely on complex sample preparation to separate the toxins from the food matrix. The method includes two steps: extraction of mycotoxins from solid to liquid phase as well as liquid to liquid phase, followed by application of cleanup procedures for boosting sensitivity and specificity of screening and quantification. Other techniques for screening are based on chemical marker capture for quantitative detection, such as ELISA and colorimetric kits, which typically require specialized reagents, equipment, and trained personnel as well as long lead times. Some rapid screening kits include lateral flow dipstick (LFD) kits, and flow through devices that use visual immunological responses; however, these are capable only of performing highly simplistic qualifications with low limit range or accuracy problems.

In addition to pathogens and metabolites, chemical and synthetic agents found in the environment from human-activity derived pollution can also be detrimental to human health. For example, exposure to pesticides, which include herbicides, fungicides, insecticides, disinfectants, and antimicrobials, is wide-ranging and persistent. Yet, some of them have significant toxicity, including possible carcinogenicity, endocrine disruption and hormone modulation/imbalance, non-alcoholic fatty liver disease, reproductive issues, birth related complications and celiac disease, according to peer-reviewed scientific studies.

Currently available analytical and screening techniques for detecting pesticides include chromatography with mass spectrometry, which is typically reliant on complex equipment such as chromatography columns coupled with spectrometer detectors, and specialty reagents for phasal extraction of the samples. Not only do these requirements add to pre-processing steps and time, but they also require complex reagents and standards particular to each food type and water sample. Such multi-step processing, extraction and derivatization steps for analysis or screening severely limit their overall ability to perform in-situ, large-scale detection, or monitoring. Other techniques for screening are based on ELISA-like assays and colorimetric kits, which are either expensive, or error-prone, as discussed previously. In addition, due to their wide variety, detecting toxic chemical and synthetic agents is not trivial and requires a multi-analyte testing strategy for lower costs and efficacy.

Another type of contaminant that is regulated by governmental bodies worldwide is genetically modified organisms (GMO) based food from crops and crop products. Currently, genetically modified food products are manufactured and distributed abundantly worldwide. The concerns associated with the use of genetically modified foods are based on food safety and nutritional value with respect to non-GMO foods. A study conducted by Pew Research Center in 2015 indicated that 57% of consumers perceive consumption of GMO foods to be unsafe while 37% concur with the safety value of GMO food. Based on a report from the National Academy of Sciences in the United Kingdom published in 2016, GMO food consumption include risks from cancers, kidney disease, obesity, celiac disease, diabetes, and allergies. Hence, different regulatory bodies have developed frameworks to quantify, trace and label GMO presence in crop and food products. For example, The United States Food and Drug Administration requires that food makers, importers, and certain retailers label foods that are bioengineered or have bioengineered ingredients that have been tested by pre-approved screening methods.

Current testing and quantification for detection and identification of GMO in food are based on two approaches: DNA detection and protein detection. DNA detection includes real-time Polymerase Chain Reaction (PCR), multiplex PCR, and multiplex real-time PCR, all of which need complex equipment and reagents and therefore are costly. Protein detection relies on proteins derived from GMOs, which can vary depending on the food type. Thus, current methods of detection tailored towards detecting and/or quantifying a single protein will not work if the food sample contains multiple types of proteins, all of which need to be detected and quantified.

Another type of environmental pollutant is derived from plastics: persistent organic pollutants (POPs) include dichloro-diphenyl-trichloro-ethane (DDT), polychlorinated biphenyls (PCBs), per- and polyfluorinated alkyl substances (PFAS), Phthalates and Bisphenols (BPs). These are highly toxic, yet abundant due to their use in a wide range of industries, such as manufacturing of cookware, fire retardants, cosmetics, paints, toys; packaging industries for food wrappers and pharmaceuticals; and fuel and energy industry and agrochemicals. In particular, PFAS are hazardous and have been shown to be carcinogenic; additionally, exposure to PFAS is linked to other detrimental health effects such as elevated cholesterol, obesity, weakened immune system, as well as endocrine disruption. Because classification of PFAS is based on the presence of perfluorosulfonic acid (PFSA) or perfluorocarboxylic acid (PFCA), currently available detection platforms probe for the presence of organic fluorine chemical markers in water and food samples. The current method of analysis for PFAs is based on combustion ion chromatography, in which samples are combusted to break the carbon-fluorine bond. The evolution from this reaction is then transferred to an ion chromatograph for analysis. The fluoride is measured in the presence of internal standards to calibrate the analytical results. Additional techniques use chromatography in conjunction with spectrometric detection such as solid phase extraction with liquid chromatography/tandem mass spectrometry. As discussed previously, these chromatography techniques rely on complex equipment, specialty reagents, and multi-step processing, which can result in high costs and long lead times.

Bisphenols are heavily used in the production of polycarbonate products, resins, and epoxies; they are characterized by the presence of dual-hydroxyphenyl end groups. Bisphenols are known to be endocrine disruptors that can cause irreversible damage to human health, including to-sexual differentiation, brain development, and immunologic function, especially in infants and children. Bisphenols are found in different structural analogues that are utilized for similar functionalities, among which the most widely found bisphenol analogues are: Bisphenol A (BPA), Bisphenol S (BPS), Bisphenol F (BPF). Currently available methods to detect bisphenols include, chromatography, fluorescence spectrophotometry and capillary electrophoresis. These methods rely on complex equipment, specialty reagents, and multi-step processing, which can result in high costs and long lead times.

Phthalates, in particular phthalic acid, are used insecticides, cosmetics, plastics and as additives, stabilizers and softeners in many consumer and industrial products. Health hazards associated with phthalates include lowering of testosterone and abnormalities in the male reproductive system. Current methods of detection include gas chromatography-mass spectrometry, liquid chromatography, and liquid chromatography/tandem mass spectrometry. As discussed previously, these methods rely on complex equipment, specialty reagents, and multi-step processing, which can result in high costs and long lead times.

In addition to these environmental contaminants, there is also an interest in testing for food allergens, such as milk, eggs, fish, crustacean shellfish, tree nuts, peanuts, wheat, soybeans and sesame. Due to the wide variety of these foods, there are no methods currently available to rapidly and effectively test for more than one of these allergens at a time.

Accordingly, embodiments of the present disclosure present a multiplexed electrochemical biosensor that can screen for contaminants from biological, plastic, and other chemical/synthetic agent sources in samples prepared simply from aqueous runoff, food complex, water media, soil and other environmental matrices. In some embodiments, up to 16 analytes of different groups can be screened together. The multi-modal electrochemical method utilized direct current in some modes and alternating current in other modes. In various embodiments, the system as disclosed herein uses a semiconducting nanostructure thin-film on a gold based working electrode stack. The semiconducting nanostructure functions as an electrode surface for binding by affinity capture probes tailored for particular analytes. The semiconducting nanostructure also facilitates signal transduction for electrochemical methods of measurements at the electrodes.

Various embodiments of the system disclosed herein provide real-time and rapid, quantitative driven methods for screening pathogens, pollutants, and other contaminants. In various embodiments, the system includes a hand-held test device that can provide a yes/no determination for detecting the presence of specific contaminants. In some embodiments, the system can also (or alternatively) provide a quantifiable measurement of the contaminant without relying on complex supporting equipment or multi-step processes.

In some examples, the system uses a label-free detection strategy for measuring multiple contaminants directly in samples with minimal pre-processing. The system can measure, using a single electrode strip, a variety of contaminants, including biological pathogens, synthetic and chemical agents, plastic pollutants and food allergens. The biological pathogens that can be detected include enteric viruses, parasites, and bacteria. Viral targets include Hepatitis A, Norovirus, Poliovirus, Rotavirus and Coxsackievirus. Parasite targets include Giardia, Cryptosporidium, Schistosoma, Entamoeba histolytica and Cyclospora. Bacterial targets include Shiga Toxigenic *Escherichia coli* (STEC), Listeria monocytogenes, *Salmonella*, Coliforms and Campylobacter. The system as disclosed herein can also screen and quantify numerous pesticides, GMO agents and crystalline toxins in food, water, and different environmental samples. Various embodiments of the system can detect different plastic groups based on their physical characteristics and/or chemical functional groups. The system as disclosed may also track food allergens that include dairy, animal products and plant products.

In the following detailed description, various aspects of the illustrative implementations may be described using terms commonly employed by those skilled in the art to convey the substance of their work to others skilled in the art.

The term "connected" means a direct connection (which may be one or more of a communication, mechanical, and/or electrical connection) between the things that are connected, without any intermediary devices, while the term "coupled" means either a direct connection between the things that are connected, or an indirect connection through one or more passive or active intermediary devices.

The term "computing device" means a server, a desktop computer, a laptop computer, a smartphone, or any device with a microprocessor, such as a central processing unit (CPU), graphical processing unit (GPU), or other such electronic component capable of executing processes of a software algorithm.

The description uses the phrases "in an embodiment" or "in embodiments," which may each refer to one or more of the same or different embodiments.

Although certain elements may be referred to in the singular herein, such elements may include multiple sub-elements. For example, "a computing device" may include one or more computing devices.

Unless otherwise specified, the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

In the following detailed description, reference is made to the accompanying drawings that form a part hereof, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense.

The accompanying drawings are not necessarily drawn to scale. In the drawings, same reference numerals refer to the same or analogous elements shown so that, unless stated otherwise, explanations of an element with a given reference numeral provided in context of one of the drawings are applicable to other drawings where element with the same reference numerals may be illustrated. Further, the singular and plural forms of the labels may be used with reference numerals to denote a single one and multiple ones respectively of the same or analogous type, species, or class of element.

Note that in the figures, various components are shown as aligned, adjacent, or physically proximate merely for ease of illustration; in actuality, some or all of them may be spatially distant from each other. In addition, there may be other components, such as routers, switches, antennas, communication devices, etc. in the networks disclosed that are not shown in the figures to prevent cluttering. Systems and networks described herein may include, in addition to the elements described, other components and services, including network management and access software, connectivity services, routing services, firewall services, load balancing services, content delivery networks, virtual private networks, etc. Further, the figures are intended to show relative arrangements of the components within their systems, and, in general, such systems may include other components that are not illustrated (e.g., various electronic components related to communications functionality, electrical connectivity, etc.).

In the drawings, a particular number and arrangement of structures and components are presented for illustrative purposes and any desired number or arrangement of such structures and components may be present in various embodiments. Further, unless otherwise specified, the structures shown in the figures may take any suitable form or shape according to various design considerations, manufacturing processes, and other criteria beyond the scope of the present disclosure.

Figure 11:
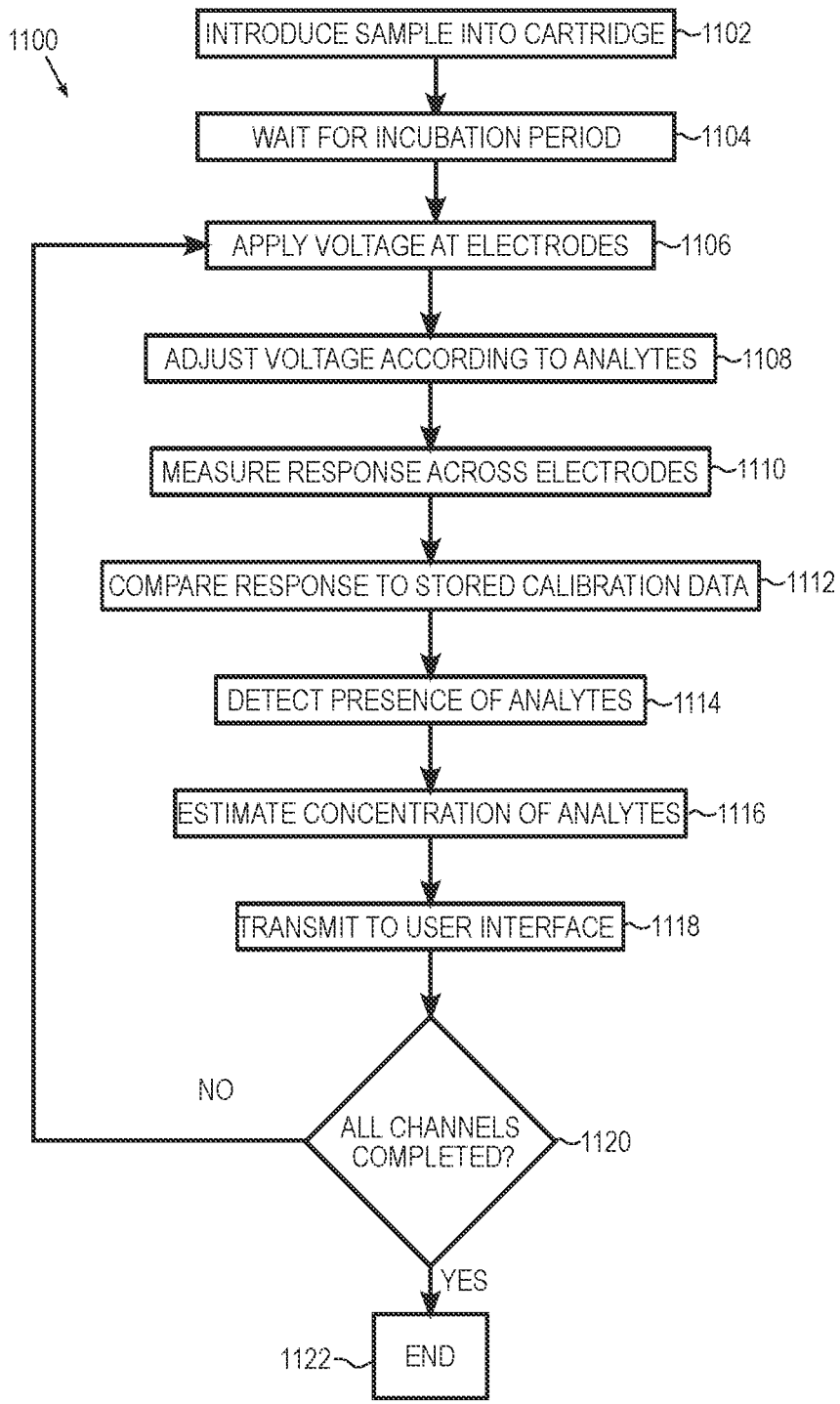
FIG. 11 is a simplified flow diagram illustrating example operations associated with a system for multi-modal and multiplexed electrochemical detection and reporting of environmental contaminants, according to some embodiments of the present disclosure.

For convenience, if a collection of drawings designated with different letters are present (e.g., FIGS. 11A-11G), such a collection may be referred to herein without the letters (e.g., as "FIG. 11"). Similarly, if a collection of reference numerals designated with different letters are present (e.g., 106a, 106b), such a collection may be referred to herein without the letters (e.g., as "106") and individual ones in the collection may be referred to herein with the letters. Further, labels in upper case in the figures (e.g., 106A) may be written using lower case in the description herein (e.g., 106a) and should be construed as referring to the same elements.

Various operations may be described as multiple discrete actions or operations in turn in a manner that is most helpful in understanding the claimed subject matter. However, the order of description should not be construed as to imply that these operations are necessarily order dependent. In particular, these operations may not be performed in the order of presentation. Operations described may be performed in a different order from the described embodiment. Various additional operations may be performed, and/or described operations may be omitted in additional embodiments.

Example Embodiments

FIG. 1A is a simplified block diagram illustrating an example electrode strip 100 for multi-modal and multi-plexed electrochemical detection and reporting of environmental contaminants, according to some embodiments of the present disclosure. Electrode strip 100 comprises a substrate 102 having conductive pathways (not shown). A first portion of substrate 102 (proximate to a first end) is encased in a cartridge 104. A second portion of electrode strip 100 comprises a handling region 110 between cartridge 104 and a third portion (proximate to another end of substrate 102) comprising conductive contact pads 112. In various embodiments, substrate 102 may comprise a printed circuit board (PCB). In some embodiments, substrate 102 may comprise a flexible polyimide ribbon. In other embodiments, substrate 102 may comprise rigid or flexible materials, such as silicon, glass, polyurethane, polycarbonate, polyamide, polyimide, paper, membrane polymer (e.g., nitrocellulose, polyvinylidene fluoride, nylon, polyethersulfone, etc.) and the like.

In some embodiments, the first portion, the second portion and the third portion of substrate 102 may comprise a continuous material system. For example, substrate 102 may comprise a PCB, which extends from the first portion to the third portion continuously. In other embodiments, first portion, second portion and third portion of substrate 102 may comprise dissimilar materials. For example, the first portion may be formed of a rigid glass material, and the second portion and the third portion may comprise a PCB suitably directly connected to the first portion. Various other such configurations are included within the broad scope of the embodiments.

Cartridge 104 comprises a fluid inlet 106 and a plurality of vent holes 108. In some embodiments, fluid inlet 106 may be in the center of cartridge 104. In other embodiments, fluid inlet 106 may be elsewhere in cartridge 104 without departing from the scope of the disclosure. In some embodiments, cartridge 104 functions as a sleeve to facilitate uniform dispersion of the sample and contain the sample within an enclosed space, as described in further detail in FIG. 1C. Handling region 110 may be large enough to facilitate ease of handling electrode strip 100, for example, by a human operator. Handling region 110 may be sized to permit pick and place by hand, and to facilitate writing (or affixing) sample labels, etc. Conductive contact pads 112 may facilitate interfacing with other electronic components comprising sensing circuitry, electronic processing etc. for readout and analysis.

Figure 1B:
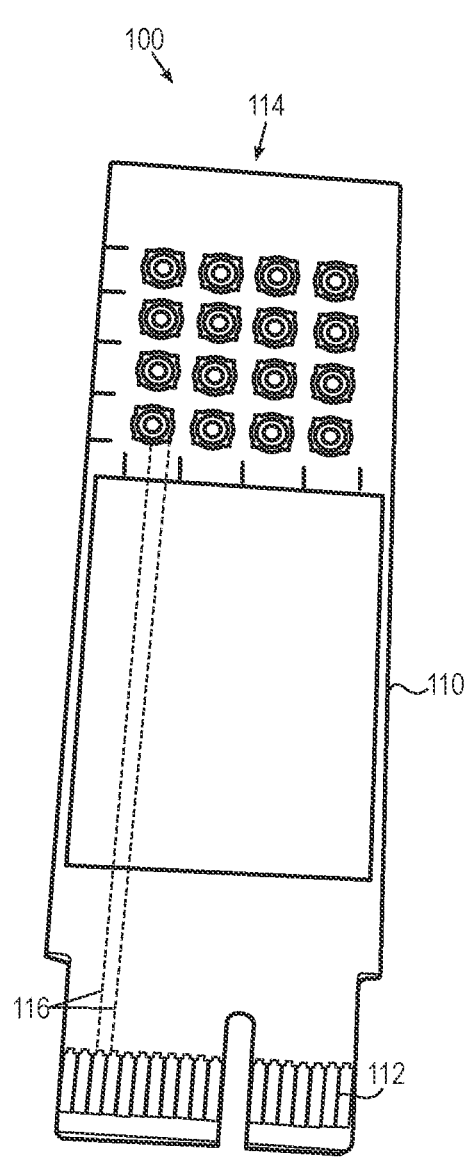

FIG. 1B is a simplified block diagram showing electrode strip 100 with cartridge 104 removed, exposing a plurality of sensors 114 (also referred to in the singular as sensor 114) configured to be in direct contact with the sample contained within cartridge 104. Each sensor 114 may be conductively coupled to at least a pair of conductive contact pads 112 by conductive pathways 116 shown in dotted lines. In various embodiments, conductive pathways 116 may comprise metal lines (e.g., copper traces) and metal vias in substrate 102. In various embodiments, the sensing circuitry external to electrode strip 100 and conductively coupled to sensors 114 through contact pads 112 may be configured to detect changes to electron and ion mobility and charge accumulation in the presence of analytes in the sample and determine the presence and concentration of the analytes based on the detected changes.

Figure 1C:
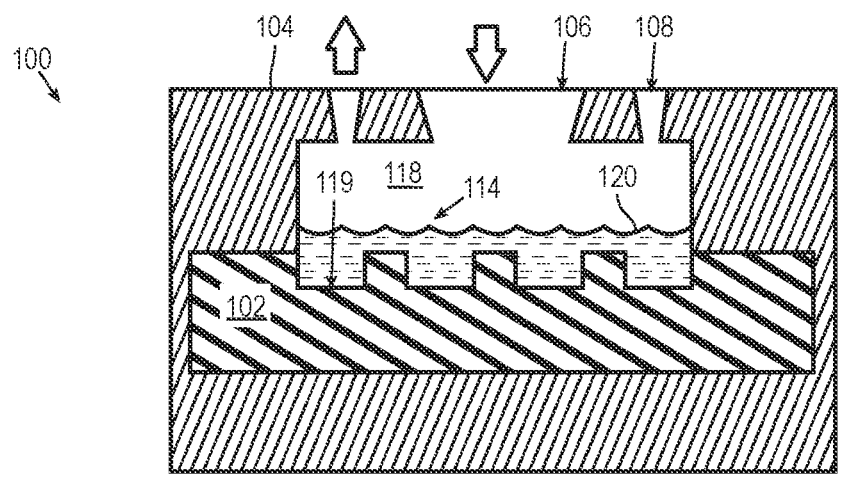

FIG. 1C is a simplified block diagram illustrating a cross-section of electrode strip 100 along axis C-C' of FIG. 1A. Cartridge 104 may surround substrate 102 in some embodiments. Cartridge 104 may include an enclosed space 118 over plurality of sensors 114. In some embodiments, enclosed space 118 may include electrode wells 119 over each sensor 114. Electrode wells 119 function as a well (e.g., support, container, etc.) holding the sample in place on surface of electrodes 122. Enclosed space 118 may facilitate containing (e.g., enclosing, holding, etc.) a sample 120 so that sample 120 comes in direct contact with sensors 114. Sample 120 is introduced into enclosed space 118 through fluid inlet 106. In various embodiments, the location of fluid inlet 106 is such that sample 120 is approximately uniformly distributed over sensors 114. As sample 120 enters enclosed space 118, air in enclosed space 118 may exit out of cartridge 104 through vent holes 108.

Figure 1D:
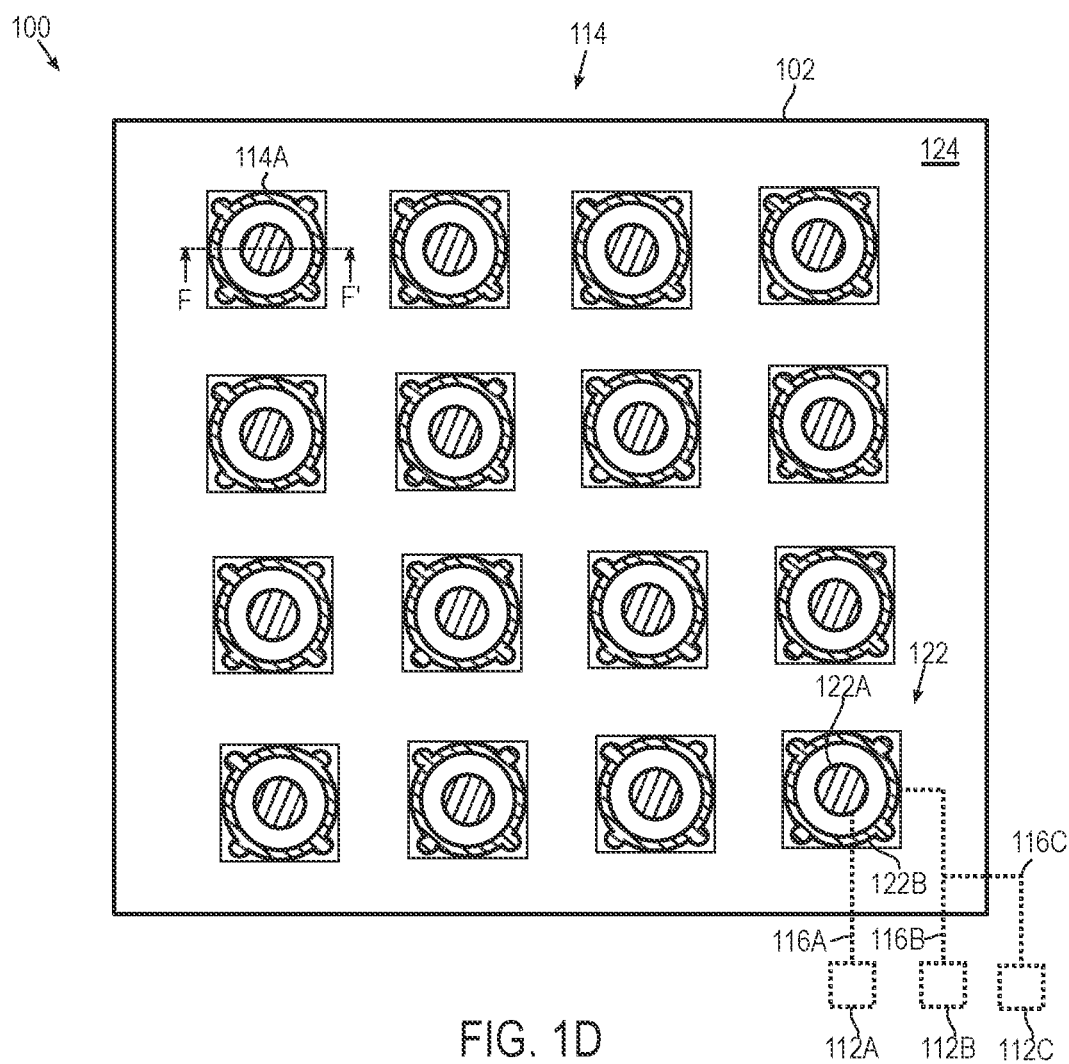

FIG. 1D is a simplified block diagram illustrating example details of electrode strip 100, showing plurality of sensors 114, according to some embodiments of the present disclosure. In some embodiments, plurality of sensors 114 may be arranged in an array. In some other embodiments, plurality of sensors 114 may be arranged in a honeycomb pattern. Any suitable arrangement of sensors 114 may be included without departing from the scope of the embodiments herein. Each sensor 114 comprises a plurality of electrodes 122. In some embodiments, plurality of electrodes 122 comprises a first electrode 122a and a second electrode 122b at least partially surrounding first electrode 122a. In some embodiments, first electrode 122a is a working electrode and second electrode 122b is a reference electrode. During operation, voltage is applied between first electrode 122a and second electrode 122b. In the embodiment shown, first electrode 122a and second electrode 122b may be approximately circular and concentric, with first electrode 122a being a circle and second electrode 122b being concentric and approximately annular around first electrode 122a. First electrode 122a and second electrode 122b in contact with sample 120 may collectively form an electrochemical cell.

First electrode 122a and second electrode 122b may be separately conductively coupled to conductive contact pads 112a and 112b by respective conductive pathways 116a and 116b. In some embodiments, conductive pathway 116b may be conductively coupled to another conductive pathway 116c connected to conductive contact pad 112c. Conductive contact pad 112a may be referenced by a sensing circuitry (not shown) as a working electrode; conductive contact pad 112b may be referenced by the sensing circuitry as a reference electrode, and conductive contact pad 112c may be referenced by the sensing circuitry as a counter electrode in some embodiments. Each sensor 114 may be surrounded by solder mask 124 that serves to provide electrical isolation from other sensors 114.

In some embodiments, second electrode 122b of sensors 114 may be conductively coupled to a common contact pad 112 so that the same voltage may be applied thereto. In some other embodiments, second electrode 122b of sensors 114 may be conductively coupled to respective contact pads 112 even though the same voltage is applied to both. In yet other embodiments, second electrode 122b of sensors 114 may have different voltages applied respectively thereto.

Figure 1E:
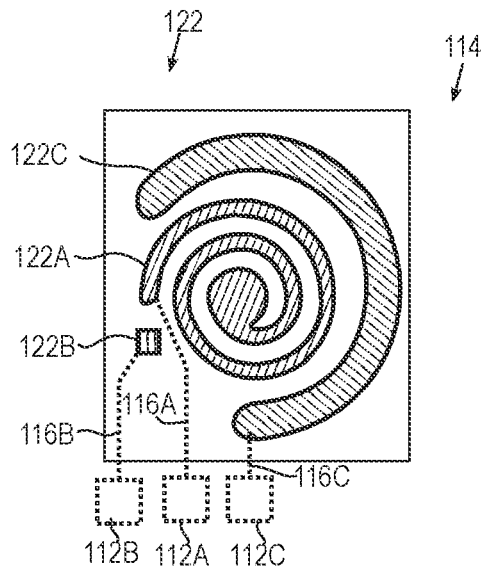

In another embodiment, as shown in FIG. 1E, sensor 114 may comprise three electrodes 122a, 122b and 122c. First electrode 122a may be the working electrode, second electrode 122b may be the reference electrode and third electrode 122c may be the counter electrode. Each electrode 122a, 122b and 122c may be conductively coupled to contact pads 112a, 112b and 112c respectively by conductive pathways 116a, 116b and 116c. During operation, bias voltage is applied between first electrode 122a and second electrode 122b. Third electrode 122c acts as source or sink for the excess current, helping to reduce resistance at the surface of first electrode 122a, thereby serving to increase the sensitivity of sensor 114. In the embodiment shown, electrodes 122a, 122b and 122c may be concentric circular interdigitated elements, with first electrode 122a having a spiral shape. In some embodiments, first electrode 122a may comprise gold, second electrode 122b may comprise silver or silver chloride, and third electrode 122c may comprise carbon.

In some embodiments, all sensors 114 in electrode strip 100 may comprise two electrodes 122a and 122b only as shown in FIG. 1C; in some other embodiments, all sensors 114 in electrode strip 100 may comprise three electrodes 122a, 122b and 122c as shown in FIG. 1D; in yet other embodiments, a subset of sensors 114 may comprise two electrodes 122a and 122b, and another subset of sensors 114 may comprise three electrodes 122a, 122b and 122c.

Figure 1F:
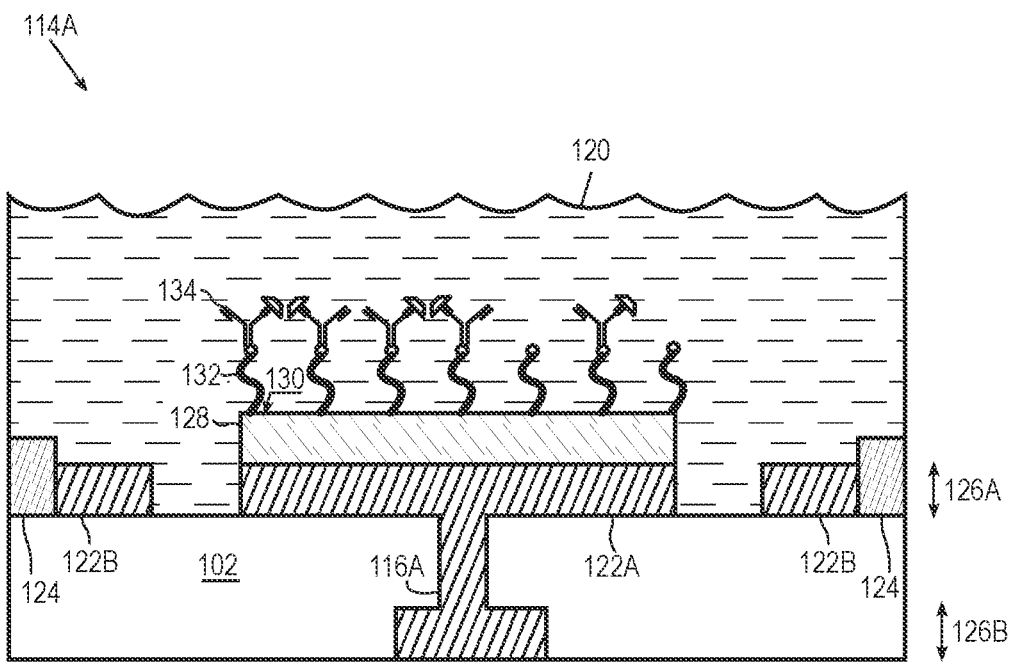

FIG. 1F is a simplified cross-sectional diagram illustrating details of example sensor 114A in electrode strip 100 along axis F-F' as shown in FIG. 1D, according to some embodiments of the present disclosure. Substrate 102 may comprise multiple layers 126 of conductive pathways surrounded by dielectric layers such as polyimide, glass fiber-reinforced epoxy (FR4), etc. First electrode 122a and second electrode 122b may be concentric and coplanar on a first layer 126a of substrate 102. In various embodiments, electrodes 122 may comprise any suitable conducting material, such as copper or gold, which does not react with sample 120.

Conductive pathway 116a in direct contact with first electrode 122a may comprise a metal via that connects first electrode 122a to a metal line in a different layer 126b of substrate 102. Other conductive pathways 116b (not shown) in first layer 126a may conductively couple second electrode 122b to corresponding conductive contact pad 112b. In some such embodiments, conductive contact pad 112a may be in second layer 126b of substrate 102, and conductive contact pad 112b may be in first layer 126a of substrate 102. Although only one sensor 114a is shown here, such is only for example purposes; it may be understood that substantially all sensors 114 in electrode strip 100 may have the same or similar configuration.

First electrode 122a, which is the working electrode, may be coated with an active sensing element 128. In some embodiments, active sensing element 128 may comprise a semiconductor thin-film (e.g., nanomaterial and other modifications). In a general sense, the properties of the semiconducting material depend on a number of electrons in that material available to move freely through the material under the influence of an externally applied electric field. Any suitable semiconducting material appropriate to the assay protocol may be used within the broad scope of the embodiments.

Non-limiting examples of semiconducting materials that can be used in active sensing element 128 may include the following: Diamond, Silicon, Germanium, Gray tin (aSn), Sulfur (aS), Gray selenium, Tellurium, Silicon carbide {3CSiC), Silicon carbide (4HSiC), Silicon carbide (6HSiC), Boron nitride (cubic), Boron nitride (hexagonal), Boron nitride (nanotube), Boron phosphide, Boron arsenide, Aluminium nitride, Aluminium phosphide, Aluminium arsenide, Aluminium antimonide, Gallium nitride, Gallium phosphide, Gallium, arsenide, Gallium antimonide, Indium nitride, Indium, phosphide, Indium arsenide, Indium antimonide, Cadmium selenide, Cadmium, sulfide, Cadmium telluride, Zinc oxide, Zinc selenide, Zinc sulfide, Zinc telluride, Cuprous, chloride, Copper sulfide, Lead selenide, Lead(II) sulfide, Lead telluride, Tin sulfide, Tin sulfide, Tin telluride, Bismuth, telluride, Cadmium phosphide, Cadmium arsenide, Cadmium antimonide, Zinc phosphide, Zinc arsenide, Zinc antimonide, Titanium dioxide (anatase), Titanium dioxide (rutile), Titanium dioxide (brookite), Copper (I) oxide, Copper(II) oxide, Uranium, dioxide, Uranium, trioxide, Bismuth, trioxide, Tin dioxide, Lead(II) iodide, Molybdenum disulfide, Gallium, selenide, Tin sulfide, Bismuth sulfide, Iron(II) oxide, Nickel(II) oxide, Europium(II) oxide, Europium(II) sulfide, Chromium(III) bromide, Arsenic sulfideOrpiment, Arsenic sulfideRealgar, Platinum, silicide, Bismuth(III) iodide, Mercury(II) iodide, Thallium(I) bromide, Silver sulfide, Iron disulfide, Lead tin, telluride, Thallium tin telluride, Thallium germanium telluride, Barium titanate, Strontium, titanate, Lithium niobate, Lanthanum copper oxide, Gallium manganese arsenide, Indium manganese arsenide, Cadmium manganese telluride, Lead manganese telluride, Copper indium selenide (CIS), Silver gallium sulfide, Zinc silicon phosphide, Copper tin sulfide (CTS), Lanthanum calcium manganite, Copper zinc tin sulfide (CZTS), or Copper zinc antimony sulfide (CZAS).

Non-limiting examples of semiconductor alloy materials that can be used in active sensing element 128 include the following: Silicon-germanium, Silicontin, Aluminium gallium arsenide, Indium gallium arsenide, Indium gallium phosphide, Aluminium indium arsenide, Aluminium indium antimonide, Gallium arsenide nitride, Gallium arsenide phosphide, Gallium arsenide antimonide, Aluminium gallium nitride, Aluminium gallium phosphide, Indium gallium nitride, Indium arsenide antimonide, Indium gallium antimonide, Cadmium zinc telluride (CZT), Mercury cadmium telluride, Mercury zinc telluride, Mercury zinc selenide, Aluminium gallium indium phosphide, Aluminium gallium arsenide phosphide, Indium gallium arsenide phosphide, Indium gallium arsenide antimonide, Indium arsenide antimonide phosphide, Aluminium indium arsenide phosphide, Aluminium gallium arsenide nitride Indium gallium arsenide nitride, Indium aluminium arsenide nitride, Gallium arsenide antimonide nitride, Copper indium gallium selenide (CIGS), Gallium indium nitride arsenide antimonide, or Gallium indium arsenide antimonide phosphide.

Note that although active sensing element 128 is shown as a bulk material, in actuality, it comprises nanrorods or nanopillars of the semiconductor thin-film material. For example, where active sensing element 128 is zinc oxide, the semiconductor thin-film material may be grown on first electrode 122a using low temperature aqueous hydrothermal growth mechanisms. The nanostructures may be formed having different shapes, sizes, dimensions, and/or aspect ratios depending on the growth conditions. In some embodiments, the zinc oxide nanostructures may be grown by tuning the chemical reactions between the precursors Zn(NO3)2.6H2O and Hexamethylenetetramine (HMTA) dissolved in water. The thermal decomposition and hydrolysis reactions of these precursors results in the formation of zinc hydroxyl species which upon dehydration form zinc oxidenuclei. Pre-seeded regions on the working electrodes can then act as nucleation sites for the aligned growth of zinc oxide nanostructures.

In some other embodiments, active sensing element 128 may comprise a room temperature ionic liquid (RTIL) thin-film including organic cations and inorganic anions. Examples of RTIL based thin-films include bis(triflurometh-anesulphonyl)imide anion and tetra-alkyl ammonium cation with carboxylic acid functionalization, 1-ethyl-3-methyl-imidazolium bis(fluorosulfonyl)imide, N-methyl-N-propyl-pyrrolidinium bis(fluorosulfonyl)imide and 1-methyl-1-(2-methoxyethyl) pyrrolidinium bis(fluorosulfonyl)imide. The choice of a particular RTIL may be based on specific analytes 134 of interest as the properties of RTILs can be changed based on particular needs by suitably modifying their constituents (i.e., cation and anion). In some embodiments, active sensing element 128 may comprise a combination of semiconductor thin-film and RTIL thin-film as desired based on particular needs.

In some other embodiments, active sensing element 128 may include additional or alternate polarizing materials, such as gold nanoparticles, carbon-based nanomaterials, Poly(3,4-ethylenedioxythiophene) (PEDOT) or other functional polymers. The polarizing materials may be configured to polarize certain analytes 134 at surface 130 in the presence of an electric field. In some such embodiments, active sensing element 128 may entirely comprise the polarizing material (e.g., without any semiconductor thin-film or RTIL thin-film) over first electrode 122a. In some other such embodiments, active sensing element may comprise the semiconductor thin-film or the RTIL thin-film coated with the polarizing material.

In some embodiments, a surface 130 of active sensing element 128 may be functionalized (e.g., coated to change surface properties) with capture probes 132, comprising cell-specific receptor molecules that selectively bind to certain analytes 134 in sample 120. In some embodiments, prior to functionalizing with capture probes 132 comprising organic groups of molecules including thiol, carboxylic, and such other groups, surface 130 may be coated with a material such as gold for ease of functionalization. In some other embodiments, silver may be coated on surface 130 prior to deposition of capture probes 132. In some embodiments wherein capture probes 132 are absent, active sensing element 128 may be functionalized by the polarizing materials as described above.

In some embodiments, capture probes 132 may be mixed with aqueous-based carrier and deposited on surface 130 in liquid form. Capture probes 132 may bind to active sensing element 128. The carrier may include linking reagents that immobilize capture probes 132 to surface 130 of active sensing element 128. Subsequently, electrode strip 100 may be subject to lyophilization (similar to freeze-drying), during which the water molecules in the aqueous-based carrier are sublimated to gas at low temperatures and removed by vacuum without affecting capture probes 132. Thus, first electrode 122a, coated with active sensing element 128 and capture probes 132 may form a unique sensor stack suitable for detecting the presence and concentration of analytes 134 in sample 120.

In various embodiments, the system as described herein does not require a detectable label for detection of analytes 134. A detectable label may be a fluorophore, an enzyme, a quencher, an enzyme inhibitor, a radioactive label, one member of a binding pair or any combination thereof. In contrast to the systems and methods of the various embodiments disclosed herein, other known sensing devices often require a label attached to the target molecule for detection and quantification. Labeling a molecule thus can drastically change its binding properties, and the yield of the target-label coupling reaction can be highly variable, which may affect the detection of target molecules. Systems as described herein, using active sensing element 128 and capture probes 132, can facilitate label-free detection of analytes 134.

In the presence of an electric field, the binding of capture probes 132 to analytes 134 changes electron and ion mobility and charge accumulation in different regions of active sensing element 128 and sample 120 between electrodes 122a and 122b. Binding of capture probes 132 to analytes 134 may occur through electrochemical, electro-ionic, polarization, and other charge-based mechanism that causes work function tuning of the material comprising active sensing element 128, resulting in modulation of space-charge capacitance and electrical double layer capacitance with direct current, and modulation of impedance with alternating current. Note that the work function is a property of surface 130 and corresponds to a minimum energy required to remove an electron from an interior of the material comprising active sensing element 128 to a point immediately above surface 130; the term "immediately" referencing a distance that is large in atomic scale, but small in terms of electrical fields.

Tunable electron-ionic mechanisms resulting from the binding events at surface 130 may be measured and/or characterized using electrical parameters, such as current, voltage, impedance, and capacitance. In some embodiments, input voltages are applied; in other embodiments, current sources are used to generate desired voltages across first electrode 122a and second electrode 122b; in yet other embodiments, a steady state potential of different amounts is maintained across first electrode 122a and second electrode 122b. The output from sensor 114 may include impedance in some embodiments; current in other embodiments; and capacitance in yet other embodiments. In many embodiments, the change to the electron and ion mobility and charge accumulation can be detected with aid of sensing circuitry (not shown), for example, by transducing to electrical impedance and capacitance signals and analyzing appropriately. The change to the electron and ion mobility and charge accumulation can then be correlated to the presence and concentration of analytes 134 in sample 120.

In some embodiments, an affinity-based biosensing method may be implemented, according to which the overall sensor network is based on the inorganic-organic composite layer by layer (LBL) system functionalized onto the electrodes. The LBL system may comprise, by way of example and not limitation, active sensing element 128 comprising a semiconductor nanomaterial, and capture probes 132 comprising Immunoglobulin (Ig) or similar receptor bio element. The electrochemical properties of the electrochemical cell formed by electrodes 122 and sample 120 is tapped to probe the interactions due to selective binding between analytes 134 and capture probes 132. A dual-mode electrochemical approach may be utilized in this study for the affinity-based approach: (i) an electrochemical spectroscopy mapping mode to capture the interfacial interactions between the electrode capture system and analytes 134; and (ii) transient diffusion limited current measurement to probe the dynamics of interactions between capture probes 132 and analyte 134.

In some other embodiments, direct-sampling techniques may be employed, according to which capture probes 132 may be absent. Instead, analytes 134 may be detected based on polarization at surface 130 of active sensing element 128 in the presence of an electric field. Polarized electrochemical interactions such as pulsed voltammetry may be utilized for measurements, to polarize and capture analytes 134 at the electrode-sample interface (e.g., surface 130). Pulsed voltametric techniques may include Square wave (SWV) and Differential pulse (DPV) Voltammetry modes and Direct Current (DC) electrochemical techniques. In some such embodiments, based on the functional material of active sensing element 128, applied voltage and pulse bias, analytes 134 may be suitably polarized. This polarization induces and stimulates an interaction to occur between analytes 134 and active sensing element 128 at surface 130, causing peak electrical signals at different potential regions based on the particular organic molecule in sample 120 (e.g., specific voltage position signatures per organic moiety). Accordingly, in such direct-sampling method, in the absence of any capture probes 132, electrochemical interactions between active sensing element 128 and analytes 134 may be used to detect and measure analytes 134 in sample 120.

In various embodiments, electrochemical methods used to detect the presence and concentration of analytes 134 include impedimetric methods (e.g., electrochemical impedance spectroscopy (EIS)), voltametric methods (e.g., pulsed voltammetry, coulometry, amperometry, linear sweep voltammetry (LSV), cyclic voltammetry (CV)), and potentiometry methods (e.g., open circuit potential (OCP) and chronopotentiometry (CP)). In a general sense, amperometry, of which voltammetry is a subclass, involves detection of ions in a solution based on electric current or changes in electric current. In voltammetry methods, current is measured by varying the voltage applied to first electrode 118a. In chronopotentiometry, current is maintained at a fixed level over a period of time during which the voltage at first electrode 118a is measured.

In some embodiments, a modified EIS technique may be used. The modified EIS technique may distinguish electrical impedance signals and background noise at low concentrations of analytes 134 in sample 120. The sensing circuitry can be configured to analyze the electrical impedance and capacitance signals by concurrently analyzing a set of Nyquist plots obtained via the modified EIS technique and a set of Mott-Schottky plots obtained via the Mott-Schottky technique. The modified EIS technique may comprise sectioning an interfacial charge layer into a plurality of spatial dielectric z-planes along a direction orthogonal to the interface between sample 120 and active sensing element 128 and probing each of the plurality of z-planes with a specific frequency selected from a range of frequencies. Specific binding of different analytes 134 to capture probes 132 may occur at known spatial heights within the interfacial charge layer. Accordingly, the sensing circuitry can be calibrated to determine the presence and concentration of each of the different analytes 134 by measuring the capacitance and impedance changes at specific frequencies corresponding to their respective z-planes at the known spatial heights within the interfacial charge layer. Various such suitable methods for detecting changes to electron and ion mobility and charge accumulation may be used within the broad scope of the embodiments herein.

Figure 2A:
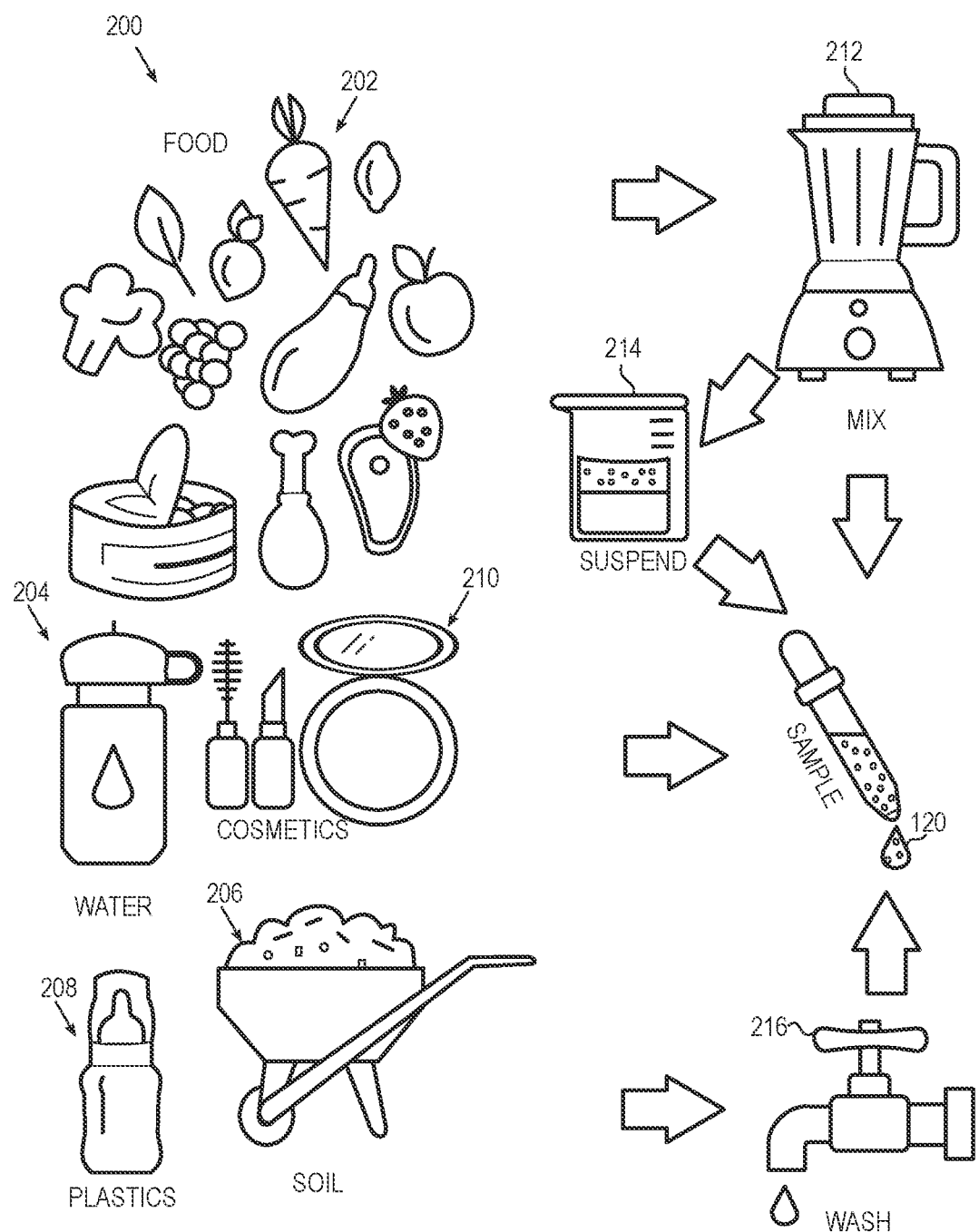
FIGS. 2A-2B are simplified block diagrams illustrating example operations in a system for multi-modal and multiplexed electrochemical detection and reporting of environmental contaminants, according to some embodiments of the present disclosure.
Figure 2B:
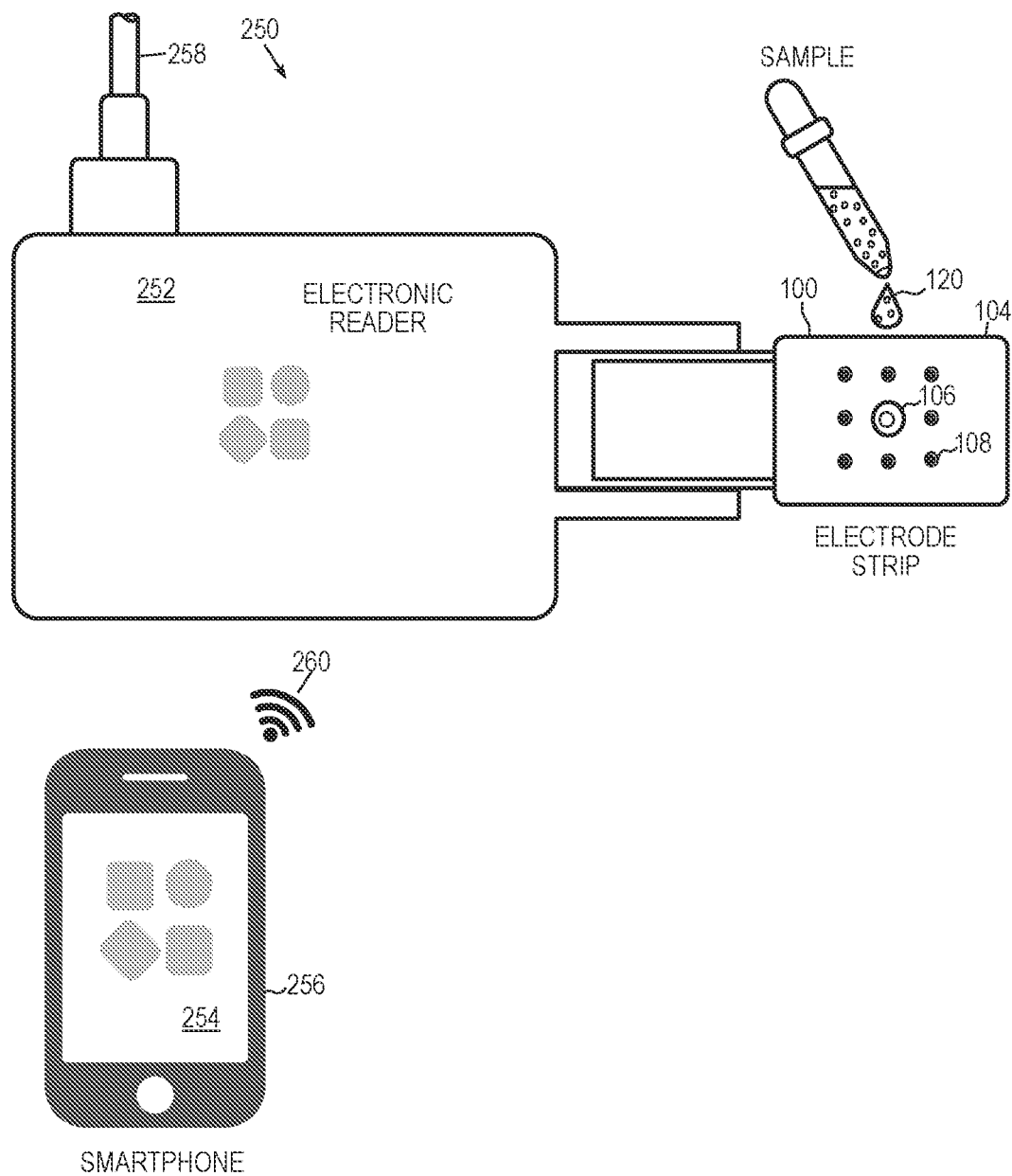

FIGS. 2A-2B are simplified block diagrams illustrating example details of the system for multi-modal and multi-plexed electrochemical detection and reporting of environmental contaminants, according to some embodiments of the present disclosure. As shown in FIG. 2A, a plurality of environmental sources 200, which may be sources of environmental contaminants, may be used to generate sample 120 for testing. Environmental sources 200 may comprise, by way of examples, and not as limitations, food 202, water 204, soil 206, plastics 208, and cosmetics 210. Other items and materials may also be included in non-human environmental sources 200 within the broad scope of the embodiments. Human-derived items, such as blood, urine, saliva, tissues, etc. are not included in environmental sources 200.

Food 202 may include, by way of examples and not as limitations, items ingested by humans by mouth, including raw, cooked, or processed (e.g., canned, semi-cooked, frozen, bagged, cut, sliced, cured, dried, juiced, powdered, pressed, aged, etc.) vegetables, fruits, dairy products, fish and/or meat, and vitamins and other supplements. Water 204 may include water from drinking water supplies, canals, wells, ponds, lakes, oceans, processed beverages (e.g., sodas, lemonades, tea, coffee, etc.). Soil 206 comprises loose surface material that covers most land, including dirt, sand, clay, mud, topsoil, and may include by way of examples and not limitations, organic matter, minerals, gases, liquids, and organisms. Plastics 208 may comprise a wide range of synthetic and semi-synthetic materials that have polymers (among other substances). Examples of plastics 208 include baby bottles, can liners, food containers, etc. Cosmetics 210 may include beauty preparations (e.g., make-up, foundation, creams, lotions, lipsticks, mascaras, powders, perfume, nail polish, etc.) and grooming aids (e.g., soaps, shampoos, toothpaste, deodorants, shaving creams, etc.)

Embodiments disclosed here allow easy and simple sample preparation compared to tedious techniques typically used to detect contaminants using other methods. For example, a common method to prepare a food matrix for detecting pesticide contamination involves micro-extraction steps using acetonitrile as a solvent followed by purification using dispersive solid phase extraction. In contrast, according to some embodiments, sample 120 may be generated from environmental sources 200 in solid forms by simply pureeing them, for example, using a blender 212. Alternatively, mixers, crushers, extractors, etc. may also be used to pulverize the solid (e.g., to lyse the cells therein) and then the crushed solids are mixed with water or a sterile saline solution such as phosphate-buffered saline (PBS) to generate a flowable slurry which may be used as sample 120. In some embodiments, the mixture may be formed by a 1:1 ratio by volume of the solids and water or saline solution. In some embodiments, large chunks of material may be filtered using a suitable strainer. For example, a salad may be blended in blender 212 and a portion thereof mixed with PBS and then filtered using a kitchen strainer and thereafter used as sample 120.

In some embodiments, after blending, the slurry may be rested until a suspension 214 is formed with two or more layers of constituents. Suspension 214 includes crushed pieces of the solid mixed with water or a saline solution such as PBS. The supernatant may be extracted from suspension 214 and used as sample 120. For example, cucumbers may be blended with PBS and then rested overnight to form suspension 214. The liquid layer that forms as a top layer of suspension 214 may be extracted and used as sample 120.

According to some other embodiments, environmental sources 200 in liquid forms may be directly used as sample 120. For example, water, coffee, milk, etc. may be used as sample 120 directly without any further processing. In a particular example, baby formula heated in a plastic bottle may be used as sample 120 to determine whether BPA has leached from the plastic bottle to the baby formula.

According to some other embodiments, environmental sources 200 in solid forms may be washed, for example, under a tap 216, and the runoff used as sample 120. For example, a head of lettuce may be washed under tap 216, and the runoff used to test for *Salmonella*. In other embodiments, environmental sources 200 may be washed in a saline solution, such as PBS and the runoff used as sample 120. Various other examples are included in the broad scope of the embodiments.

FIG. 2B is a simplified block diagram showing an example mode of operation of a system 250 for multi-modal and multiplexed electrochemical detection and reporting of environmental contaminants, according to some embodiments of the present disclosure. In various embodiments, approximately 100-120 microliters of sample 120 may be dropped into fluid inlet 106 in electrode strip 100 using a pipette, dropper, or other liquid transport device. Sample 120 may be of sufficient viscosity to enable it to flow over plurality of sensors 114 and make direct contact with electrodes 122. In many embodiments, cartridge 104 may serve to contain sample 120 in enclosed space 118 (not shown) over sensors 114. Vent holes 108 may prevent trapping of air or other gases within enclosed space 118, facilitating higher chance of contact between sample 120 and sensors 114.

In various embodiments, electrode strip 100 may be physically and conductively coupled to an electronic reader 252. Electrode strip 100 may be removable from electronic reader 252 so that electronic reader 252 can be reused for multiple tests as desired and based on particular needs, whereas electrode strip 100 may be discarded after each use. Electronic reader 252 may comprise sensing circuitry (not shown) configured to detect the presence and/or concentration of analytes 134 in sample 120. In various embodiments, the testing methodology may include a wait time (e.g., incubation period) to allow sample 120 to stabilize so that analytes 134 can bond with respective capture probes 132. The wait time may be of the order of a few minutes (e.g., ten minutes, twelve minutes, thirty minutes, etc.) and may vary depending on the nature, type, consistency and other properties of sample 120.

Electronic reader 252 may interface with an application 254 executing in a computing device 256 using wired connections 258 or wireless connections 260. In the example embodiment shown in FIG. 2B, computing device 256 is a smartphone. In other embodiments, computing device 256 may be any suitable processing device coupled to a display, such as a computer, an electronic notebook, etc. In various embodiments, sensing circuitry in electronic reader 252 may generate output signals that are interpreted suitably by application 254 and displayed appropriately in computing device 256. In some embodiments, application 254 may post-process the output signals from electronic reader 252 to collate data and generate appropriate graphs and other aids to understand the result of testing sample 120 using electrode strip 100. Electrode strip 100 may be discarded after use in various embodiments.

In various embodiments, calibration tests may be performed on various analytes 134 and the calibration data stored suitably in electronic reader 252. For example, sample 120 may comprise a liquid containing analytes 134 in a known concentration, say $C_1$. Voltages may be applied across electrodes 122 and the output measured to be, say $O_1$. The output may comprise impedance in some embodiments, or any other suitable measurement, including capacitance, current, etc. Next, the concentration of analyte 134 may be changed in sample 120 to another known concentration, say $C_2$. Voltage may be applied across electrodes 122 and the output measured to be, say $O_2$. The process may be continued until a range of concentrations has been measured, from $C_1$ to $C_N$. The pairs of outputs $O_1$-$O_N$ and analyte concentrations $C_1$ to $C_N$ at the applied voltages may be stored as calibration data in electronic reader 252 in various embodiments. The calibration data may provide an expected analyte concentration (within range $C_1$-$C_N$), for a known output (within range $O_1$-$O_N$), and vice versa. Although one particular calibration technique has been described herein, any suitable calibration technique may be used within the broad scope of the embodiments.

Figure 3:
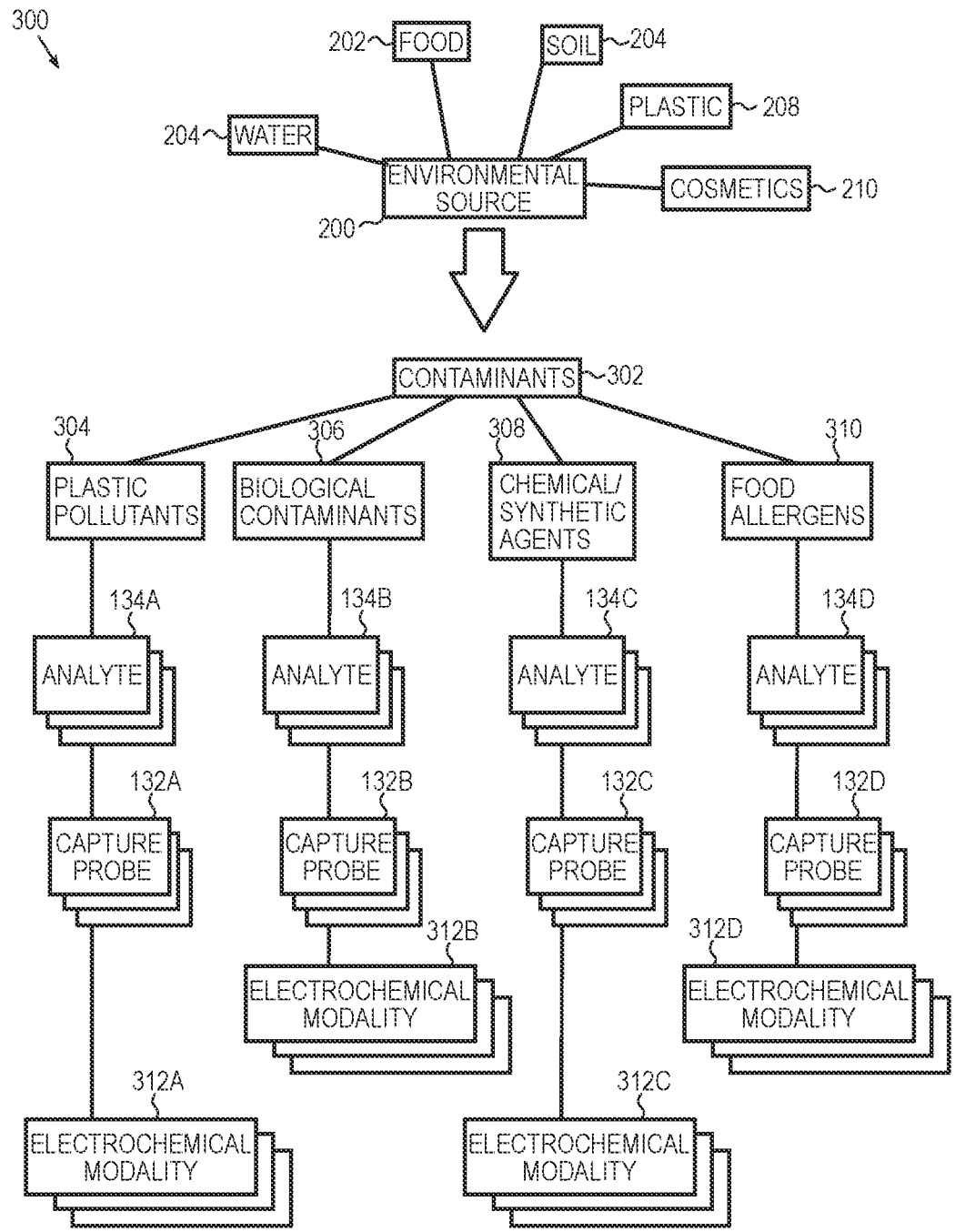
FIG. 3 is a simplified block diagram illustrating example details of a system for multi-modal and multiplexed electrochemical detection and reporting of environmental contaminants, according to some embodiments of the present disclosure.

FIG. 3 is a simplified block diagram illustrating example details 300 of operation of system 250, according to some embodiments of the present disclosure. Environmental sources 200 comprising, by way examples and not as limitations, food 202, water 204, soil 206, plastics 208 and cosmetics 210 may include one or more contaminants 302. Contaminants 302 may be classified in one example into the following categories: plastic pollutants 304, biological contaminants 306, chemical/synthetic agents 308, and food allergens 310. Note that the example classification shown is merely for explanation and is not to be construed as a limitation. Contaminants 302 may be classified in other ways, for example, into organisms (such as virus, bacteria, etc.) and non-organisms (such as BPA and pesticides); another classification may be based on sources (e.g., food-based contaminants, water-based contaminants, cosmetics-based contaminants, etc.). Various other types of classifications may be included within the broad scope of the embodiments.

The classification as shown indicates a plurality of analytes 134a-134d associated with respective categories, and corresponding capture probes 132a-132d configured to selectively bind to respective ones of analytes 134a-134d. Each combination of capture probes 132a-132d and analytes 134a-134d may indicate a specific electrochemical modality 312a-312d, suggesting different analytical approaches by sensing circuitry in electronic reader 252 to the category of contaminants 302. For example, some combinations of capture probes 132 and analytes 134 may be amenable to impedance-measurements using alternating current corresponding to a particular electrochemical modality 312, whereas other combinations of capture probes 132 and analytes 134 may be amenable to capacitance measurements using direct current corresponding to a different electrochemical modality 312.

Plastic pollutants 304 may include at least one of: (i) per- and polyfluoroalkyl substances (PFAS), (ii) bisphenols, (iii) phthalates, and (iv) polychlorinated biphenyls. Analytes 134 associated with plastic pollutants 304 include perfluorooctanoic acid (PFOA), perfluorooctane sulfonic acid (PFOS), perfluorononanoic acid (PFNA), perfluorohexane sulfonic acid (PFHxS), and perfluordecanoic acid (PFDeA). Capture probes 132a for plastic pollutants 304 may vary depending on respective analytes 134a. For example, for analytes 134a comprising organic fluorine-based markers (e.g., PFOS, PFOA, etc.), capture probes 132a may comprise molecular-imprinted polymeric (MIPS) protein receptors. For analytes 134a including BPA, BPS, and BPF, capture probes 132a may include carbon nanostructures, polymers, and covalent organic frameworks. Capture probes 132a for analytes 134a comprising phthalic acid compounds may include material systems having polymer like structures, redox molecules such as ferrocene, prussian blue, ferro-ferri cyanide, MIPs, and Azolia gel. Various other combinations of capture probes 132a and analytes 134a may be included without departing from the broad scope of the embodiments disclosed herein.

According to various embodiments, electrochemical modality 312a comprising affinity-based biosensing may be used to detect the presence and concentration of plastic pollutants 304 in environmental sources 200. The affinity-based biosensing methods may utilize an electrochemical spectroscopy mapping mode (e.g., modified EIS) to capture interfacial interactions between electrodes 122 and analytes 134a. Transient diffusion limited current measurements may be used to probe the dynamics of interaction between capture probes 132a and analytes 134a.

Biological contaminants 306 include pathogens and mycotoxins in some embodiments. Examples of analytes 134b that may be tested in system 250 for pathogens include, by way of examples and not as limitations, *Salmonella, Escherichia Coli* $O_{157}$*, Campylobacter, Listeria*, Hepatitis A, Norovirus, Poliovirus, Rotavirus, Coxsackievirus, and Coliforms. Other examples of biological contaminants 306 are mycotoxins. Analytes 134b for mycotoxins include Giardia, Cryptosporidium, Schistosoma, Entamoeba histolytica and Cyclospora. Capture probes 132b for biological contaminants 306 may vary depending on corresponding analytes 134b.

In various embodiments, system 250 may be used for point-of-use testing to detect biological contaminants 306 in environmental sources 200 before they are used. System 250 using electrode strip 100 may be configured to screen for biological contaminants 306 without any need for experts or complex machinery. A simple quantitative (e.g., concentration-based) readout may be used to correlate the presence and concentration of biological contaminants 306 in environmental sources 200. With system 250, many typical problems in qualitative screening strip kits such as measurement error, colored food samples, etc. may be avoided due to specific receptor binding and chemical interaction driven capture and tracing of biological contaminants 360. In other words, as long as analytes 134b are present in sample 120, test system 250 is configured to detect their presence and concentration irrespective of the way sample 130 has been handled.

In various embodiments, electrochemical modality 312b for detecting and measuring biological contaminants 306 may include a dual-mode electrochemical approach comprising an electrochemical spectroscopy mapping mode (e.g., modified EIS) to capture interfacial interactions between electrodes 122 and analytes 134b, and a transient diffusion limited current measurement approach to probe dynamics of interaction between capture probes 132b and analytes 134b.

Chemical/synthetic agents 308 include pesticides, for example, in water 204, soil 206, or cosmetics 210. Chemical/synthetic agents 308 also include GMOs in food 202. Analytes 134c and corresponding capture probes 132c for chemical/synthetic agents 308 may vary according to the material being tested. Electrochemical modality 312c for chemical/synthetic agents 308 may include affinity-based biosensing mechanism and contact based interfacial capture and transduction depending on the combination of capture probes 132c and analytes 134c. For example, capture probes 132c may be different for analytes 134c belonging respectively to chloro-phenoxy, organophosphate, dipyridyls, triazine and organochlorine groups. However, in a single group, electrochemical modality 312c may vary depending on corresponding analytes 134c. For example, analytes 134c comprising 2,4-Dichlorophenoxyacetic acid may be tested using same capture probes 132c as for Dicamba, which is also a chloro-phenoxy compound. However, electrochemical modality 312c for 2,4-Dichlorophenoxyacetic acid may comprise affinity-based biosensing, whereas Dicamba may also be tested by direct-sampling method using (no receptor) contact electrochemical modes.

Organophosphates such as Glyphosate, Chlorpyrifos, Malathion, and Parathion may be tested using affinity-based biosensing. Another organophosphates, namely Parathion, may be tested by direct-sampling method using contact electrochemical modes and affinity-based biosensing. Other organophosphates, such as Glufosinate and α-amino-3-hydroxy-5-methyl-4-isoxazolepropionic acid (AMPA) may use only direct-sampling method using (no receptor) contact electrochemical modes. In another example, Paraquate, which is a dipyridyls, may be tested for trace amounts by affinity-based biosensing, whereas Diquat, another dipyridyls, may be tested by direct-sampling method using (no receptor) contact electrochemical modes. Triazines, such as Atrazine and Simazone may be tested by affinity-based biosensing to detect trace amounts. Likewise, organochlorine such as Dichlorodiphenyltrichloroethane (DDT) may also be tested by affinity-based biosensing to detect trace amounts.

According to various embodiments, electrochemical modality $312c$ comprising affinity-based biosensing may utilize an electrochemical spectroscopy mapping mode (e.g., modified EIS) to capture interfacial interactions between electrodes $122$ and analytes $134c$. Transient diffusion limited current measurements may be used to probe the dynamics of interaction between capture probes $132c$ and analytes $134c$.

According to various embodiments, electrochemical modality $312c$ comprising direct-sampling, contact based electrochemical mode may utilize special metallized coatings on electrodes $122$ as discussed previously in reference to FIG. 1F. Analytes $134c$ in some such embodiments may use polarized interfacial chemistry techniques. In such embodiments, pulsed voltametric techniques (e.g., contact electrochemistry) may be used to polarize and capture analytes $134c$ at interfaces between sample $120$ and electrodes $122$.

In embodiments where chemical/synthetic agents $308$ comprise GMOs, analytes $134c$ may differ for various food types, such as GMO corn and GMO soy. For GMO corn, analytes $134$ may include Cry1A protein, CP4 EPSPS enzyme, Cry3Bb, Cry1F, Phosphinothricin-N-Acetyltransferase (PAT) enzyme, Cry2A, and Cry1Ab. (Cry refers to *Bacillus thuringiensis* (Bt) crystalline proteins) For GMO soy, analytes $134$ may include PAT enzyme and CP4 EPSPS enzyme (for example, to detect LibertyLink™ and Roundup Ready™ GMO soy products). Capture probes $132c$ may comprise suitable antibodies for protein-based analytes $134c$.

Food allergens $310$ include various types of foods with correspondingly different analytes $134d$ and respective capture probes $132d$. For example, analytes $134d$ for shellfish allergen may be Tropomyosin; for peanut allergen may be Ara h1, 2; for milk allergen may be Casein; for soy allergen may be soy protein; and so on. In some embodiments, electrochemical modality $312d$ may include using a combination of two-electrode sensors (e.g., having only electrodes $122a$ and $122b$) and three-electrode sensors (e.g., having electrodes $122a$, $122b$ and $122c$) that can facilitate a wide range of direct current based analysis and alternating current based impedance measurement techniques.

FIG. 4A-4E are simplified block diagrams illustrating example details $400$ of system $250$, according to some embodiments of the present disclosure. In various embodiments, multiple types of analytes $134$ may be detected using a single electrode strip $100$. Such multiplexing may allow quantifying multiple analytes $134$ in a single step (e.g., using a single electrode strip $100$ and sample $120$), providing advantages over individual testing through shorter processing time, lower sample volume, and reduced cost per test. Electrode strip $100$ may include a plurality of sensors $114$, with some sensors $114a$ configured to detect and measure analytes $134x$ and other sensors $114b$ configured to detect and measure other analytes $134y$. The respective outputs of sensor $114a$ and sensor $114b$ may be independently measured and transduced (e.g., amperometric or impedometric). To this end, the output electrical signals from each sensor $114a$ and $114b$ may be separately fed as channels $402a$ and $402b$ respectively to electronic reader $252$. Note that channels $402a$ and $402b$ are shown as single lines merely for ease of illustration. In actuality, they may include separate conductive traces for signal input, signal output and electrical ground. The sensing circuitry in electronic reader $252$ may be configured to individually and selectively control, activate, or modulate sensor $114a$ and sensor $114b$, for example, to aid in enhancing sensitivity of detection of different analytes $134x$ and $134y$.

In some embodiments, electrode strip $100$ may be configured to detect various types of analytes $134$ in a particular environmental source $200$. For example, sample $120$ comprising soil $206$ may be suspected of having plastic pollutants $304$ with corresponding analytes $134a$, and chemical/synthetic agents $308$ with corresponding analytes $134c$. Sensors $114$ in electrode strip $100$ may be configured with appropriate active sensing element $128a$ and $128c$, and capture probes $132a$ and $132c$ on different ones of sensors $114$ to detect analytes $134a$ and $134c$, respectively.

In another example, sample $120$ comprising cosmetics $210$ may be alleged to be contaminated with biological contaminants $306$ having analytes $134b$ and chemical/synthetic agents $308$ having analytes $134c$. Sensors $114$ in electrode strip $100$ may be configured with appropriate active sensing element $128b$, capture probes $132b$ and $132c$ on different ones of sensors $114$ to detect analytes $134a$ and $134c$, respectively.

In yet another example, sample $120$ comprising food $202$ may be tested for biological contaminants $306$ with analytes $134b$, chemical/synthetic agents $308$ having corresponding analytes $134c$, and food allergens $310$ with corresponding analytes $134d$. Sensors $114$ in electrode strip $100$ may be configured with appropriate active sensing elements $128b$, $128c$ and $12d$, and capture probes $132b$, $132c$, and $132d$ on different ones of sensors $114$ to detect analytes $134b$, $134c$, and $134d$, respectively. In such embodiments, electrode strip $100$ may be usable only for the specific environmental source $200$ and/or analytes $134$ being tested. Various such combinations are included in the broad scope of the embodiments disclosed herein.

In some embodiments, electrode strip $100$ may be configured to detect various types of analytes $134$ in various categories of contaminants $302$. For example, sample $120$ comprising biological contaminants $306$ may include analytes $134b$ comprising *Salmonella, E. Coli*, norovirus, etc. Sensors $114$ in electrode strip $100$ may be configured with appropriate active sensing element $128b$ and capture probes $132b$ for separate ones of the suspected analytes $134b$. Such electrode strip $100$ may not be usable to test for other categories of contaminants $302$, say plastic pollutants $304$. Various such combinations are included in the broad scope of the embodiments disclosed herein.

Assume, merely for the sake of explanation and not as a limitation, that electrode strip $100$ in system $250$ is configured with sensor $114a$ to test for analytes $134x$, sensor $114b$ to test for analytes $134y$, and sensor $114c$ to test for analyte $134z$. As shown by figurative representations in FIG. 4B, sample $120$ may include analytes $134x$, $134y$, and $134z$. As shown in FIG. 4C, sensor $114a$ may be provisioned with active sensing element $128x$ suitable for capture probes $132x$ that selectively bind to analytes $134x$ (but not to $134y$). As shown in FIG. 4D, sensor $114b$ may be provisioned with active sensing element $128y$ suitable for capture probes $132y$ that selectively bind to analytes $134y$ (but not to $134x$).

FIG. 4E is a simplified diagram showing an embodiment in which capture probes $132$ are absent (e.g., direct-sampling techniques are used to detect analytes $134$). In such embodiments, the combination of active sensing element $128$, voltage and bias may vary across different sensors $114$ such that different analytes $134$ are polarized in different sensors 114. For example, sensor 114c may comprise active sensing element 128z, and a voltage $V_2$ and bias $B_2$ may be applied thereto to detect analyte 134z. In some embodiments (not shown) another sensor 114d may comprise active sensing element 128x (i.e., same as sensor 114a), and a voltage Vz and bias Bz (different from voltage $V_x$ and bias $B_x$) may be applied thereto to detect analyte 134z (different from analyte 134x). Various such combinations are included within the broad scope of the embodiments herein.

Figure 5A:
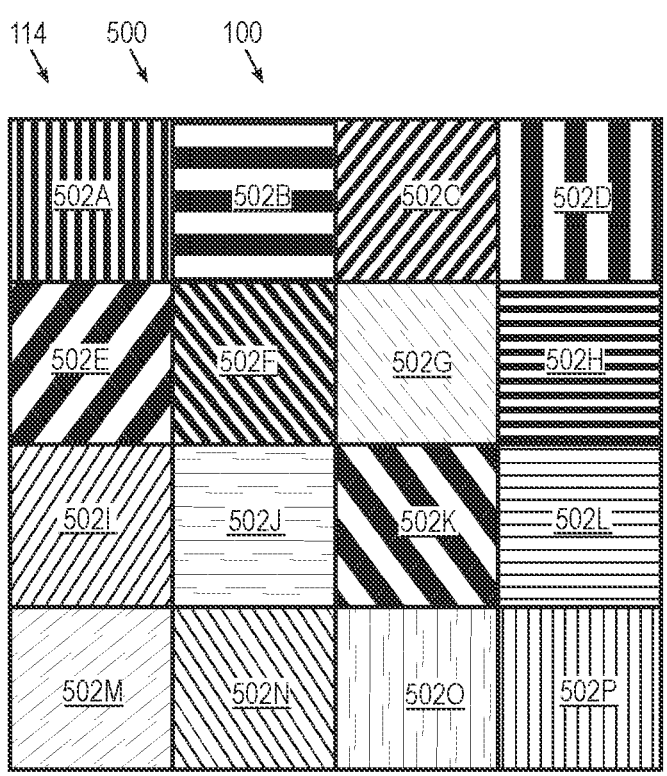
FIGS. 5A-5B are simplified block diagrams illustrating example multiplexing details of a system for multi-modal and multiplexed electrochemical detection and reporting of environmental contaminants, according to some embodiments of the present disclosure.

FIG. 5A is a simplified block diagram illustrating example multiplexing channels 500 of sensors 114 in electrode strip 100, according to some embodiments of the present disclosure. In the example embodiment shown, sensors 114 may comprise an array of 16 sensors. Note that the number of sensors 114, namely 16, is merely provided as an example and not as a limitation. Any number of sensors 114 may be included in electrode strip 100 within the broad scope of the embodiments. Each sensor 114 may comprise a pair of electrodes 122. Each pair of electrodes 122 may be collated into a single channel 502, such that 16 channels 502a-502p may be provisioned in electrode strip 100. Each channel may be configured to sense (e.g., detect presence and measure concentration) a particular one of analytes 134. Thus, electrode strip 100 as shown may facilitate sensing 16 different analytes 134 in a single sample 120.

In various embodiments, each channel may be separately excited (e.g., by applying a suitable voltage or current depending on the measurement protocol) and the corresponding response captured by electronic reader 252 and analyzed suitably. While multiplexing, where multiple analytes are detected in a single sample, is currently available in biosensor-based methods, such techniques vary widely in implementation. In one technique, multiplexing may use different quantum dots excited by the same light source to obtain different colored visualizations in one biological sample. In another example, gold and silver nanoparticles may be used to differentiate among different analytes in the same sample. In yet other techniques, different molecules can be measured at different working electrodes, but the structure of the electrodes affects measurement sensitivity and range of measurable molecules (e.g., there is no single ultimate substrate material for the fabrication of multiplexed sensors in general). Further, many of these techniques have disadvantages in terms of efficacy, sensitivity, reliability, repeatability, costs, and simplicity of use. In contrast to these methods, multiplexing using electrode strip 100 as disclosed herein can be fast, efficient, inexpensive, reliable, repeatable, and accurate.

Figure 5B:
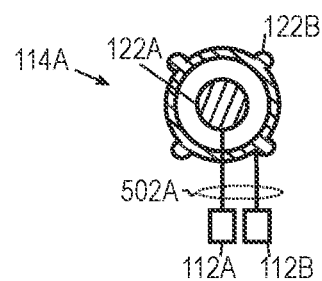

FIG. 5B is a simplified block diagram showing details of example sensor 114a comprising first electrode 122a and second electrode 122b. Conductive pathways may couple first electrode 122a and second electrode 122b to respective contact pads 112a and 112b. Although only one line and contact pad are shown for each electrode 122, such is only for example purposes so as not to clutter the drawing. Each electrode 122 may be conductively coupled to input, output and ground connections appropriately. The signals in and to sensor 114a may be collated into channel 502a for multiplexing purposes. For example, multiplexer 404 may send input signals to channel 502a, and measure output signals from channel 502a to detect presence and concentration of a particular one of analytes 134 (e.g., analytes 134a, analytes 134b, etc.) in sample 120.

Figure 6A:
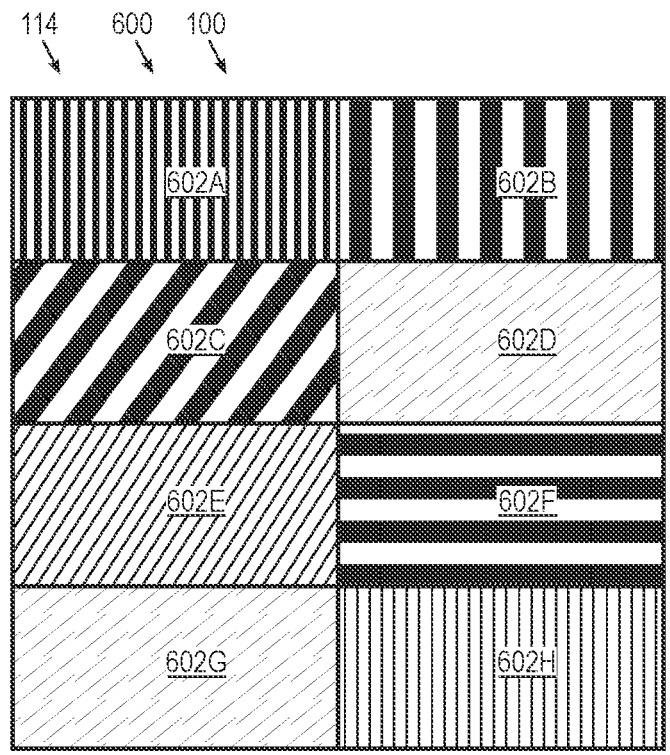
FIGS. 6A-6B are simplified block diagrams illustrating example multiplexing details of a system for multi-modal and multiplexed electrochemical detection and reporting of environmental contaminants, according to some embodiments of the present disclosure.

FIG. 6A is a simplified block diagram illustrating example multiplexing channels 600 of sensors 114 in electrode strip 100, according to some embodiments of the present disclosure. In the example embodiment shown, 16 sensors 114 may be provisioned in electrode strip 100. Each pair of sensors 114, for example, sensor 114a and sensor 114b may be collated together into a single channel 602, such that 8 channels 602a-602h may be provisioned in electrode strip 100. Each channel may be configured to sense (e.g., detect presence and measure concentration) a particular one of analytes 134. Thus, electrode strip 100 as shown may facilitate sensing 8 different analytes 134 in a single sample 120.

Figure 6B:
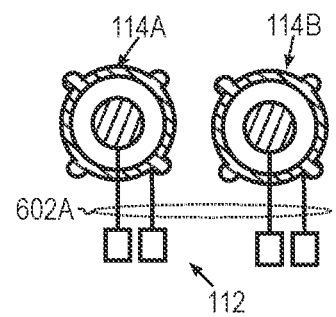

FIG. 6B is a simplified block diagram showing details of example sensor 114a and sensor 114b comprising respective electrodes. Conductive pathways may couple the electrodes to respective contact pads 112. Although only one line and contact pad are shown for each electrode 122, such is only for example purposes so as not to clutter the drawing. Each electrode 122 may be conductively coupled to input, output and ground connections appropriately. The signals in and to sensor 114a and sensor 114b may be collated into channel 602a for multiplexing purposes. For example, multiplexer 404 may send input signals to channel 602a, and measure output signals from channel 602a to detect presence and concentration of a particular one of analytes 134 (e.g., analytes 134a, analytes 134b, etc.) in sample 120.

Figure 7A:
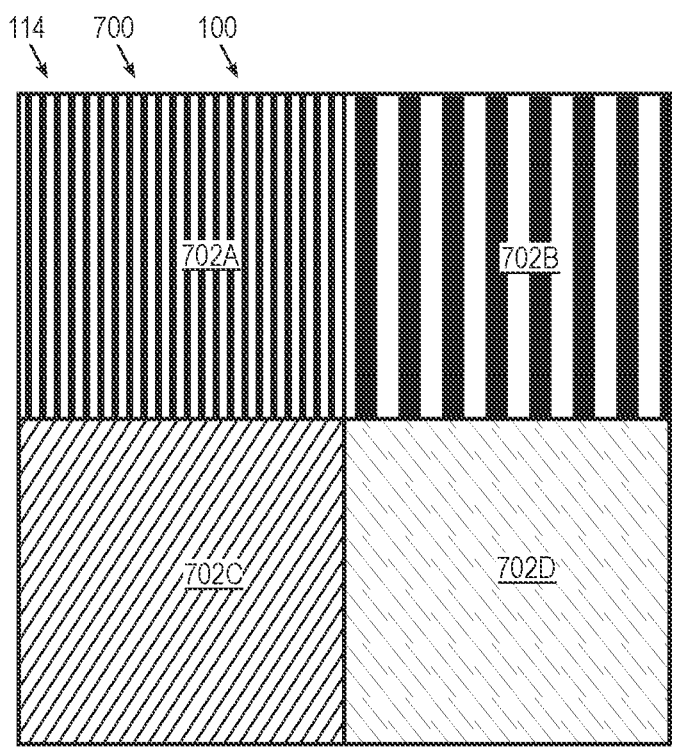
FIGS. 7A-7B are simplified block diagrams illustrating example multiplexing details of a system for multi-modal and multiplexed electrochemical detection and reporting of environmental contaminants, according to some embodiments of the present disclosure.

FIG. 7A is a simplified block diagram illustrating example multiplexing channels 700 of sensors 114 in electrode strip 100, according to some embodiments of the present disclosure. In the example embodiment shown, 16 sensors 114 may be provisioned in electrode strip 100. Each quartet of sensors 114, for example, sensor 114a, sensor 114b, sensor 114c and sensor 114d may be collated together into a single channel 702, such that 4 channels 702a-702d may be provisioned in electrode strip 100. Each channel may be configured to sense (e.g., detect presence and measure concentration) a particular one of analytes 134. Thus, electrode strip 100 as shown may facilitate sensing 4 different analytes 134 in a single sample 120.

Figure 7B:
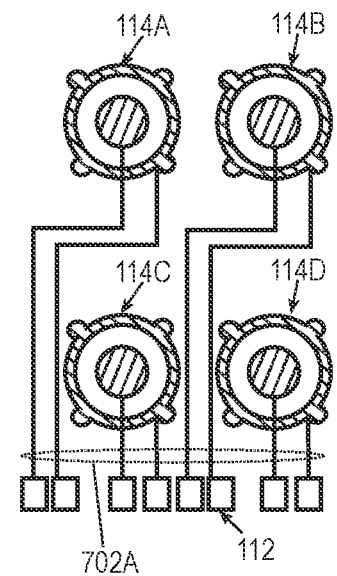

FIG. 7B is a simplified block diagram showing details of example sensors 114a-114d comprising respective electrodes. Conductive pathways may couple the electrodes to respective contact pads 112. Although only one line and contact pad are shown for each electrode 122, such is only for example purposes so as not to clutter the drawing. Each electrode 122 may be conductively coupled to input, output and ground connections appropriately. The signals in and to sensors 114a-114d may be collated into channel 702a for multiplexing purposes. For example, multiplexer 404 may send input signals to channel 702a, and measure output signals from channel 702a to detect presence and concentration of a particular one of analytes 134 (e.g., analytes 134a, analytes 134b, etc.) in sample 120.

Figure 8A:
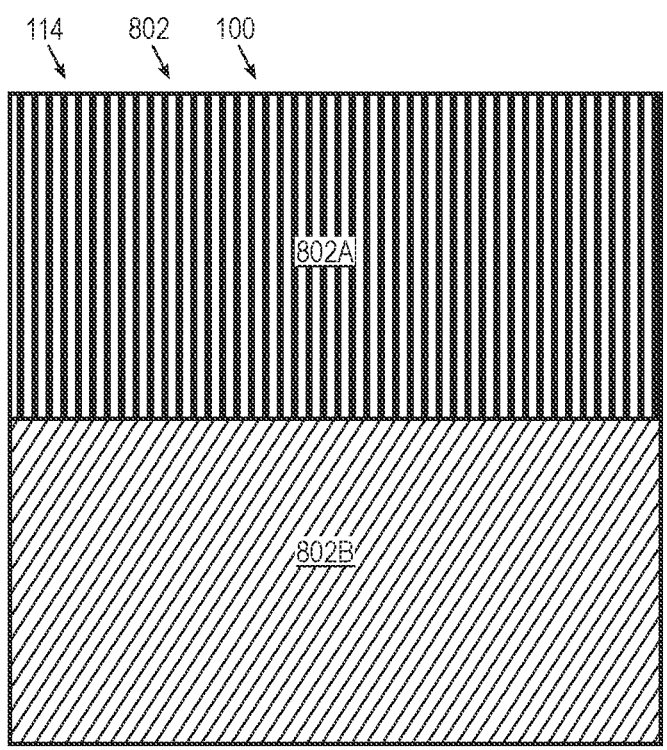
FIGS. 8A-8B are simplified block diagrams illustrating example multiplexing details of a system for multi-modal and multiplexed electrochemical detection and reporting of environmental contaminants, according to some embodiments of the present disclosure.

FIG. 8A is a simplified block diagram illustrating example multiplexing channels 800 of sensors 114 in electrode strip 100, according to some embodiments of the present disclosure. In the example embodiment shown, 16 sensors 114 may be provisioned in electrode strip 100. Each octet of sensors 114, for example, sensors 114a-114h may be collated together into a single channel 802, such that 2 channels 802a and 802b may be provisioned in electrode strip 100. Each channel may be configured to sense (e.g., detect presence and measure concentration) a particular one of analytes 134. Thus, electrode strip 100 as shown may facilitate sensing 2 different analytes 134 in a single sample 120.

Figure 8B:
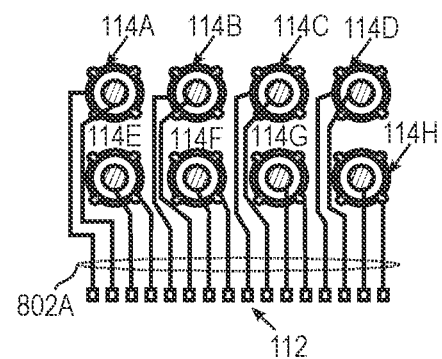

FIG. 8B is a simplified block diagram showing details of example sensors 114a-114d comprising respective electrodes. Conductive pathways may couple the electrodes to respective contact pads 112. Although only one line and contact pad are shown for each electrode 122, such is only for example purposes so as not to clutter the drawing. Each electrode 122 may be conductively coupled to input, output and ground connections appropriately. The signals in and to sensors 114a-114d may be collated into channel 802a for multiplexing purposes. For example, multiplexer 404 may send input signals to channel 802a, and measure output signals from channel 802a to detect presence and concentration of a particular one of analytes 134 (e.g., analytes 134a, analytes 134b, etc.) in sample 120.

Note that suitable combinations of the multiplexing schemes described in FIGS. 5A-8B may be implemented in various embodiments. For example, channels 802B may be further subdivided into a plurality of channels according to any one of the modulation schemes described in reference to FIGS. 5A-7B. Thus, instead of 2 channels, there may be 9 channels (1 channel corresponding to 802A and 8 channels corresponding to other 8 sensors); or 5 channels (1 channel corresponding to 802A and 4 channels corresponding to other 8 sensors); or 3 channels (1 channel corresponding to 802A and 2 channels corresponding to other 8 sensors). Various other such combinations are also included within the broad scope of the embodiments herein.

Figure 9:
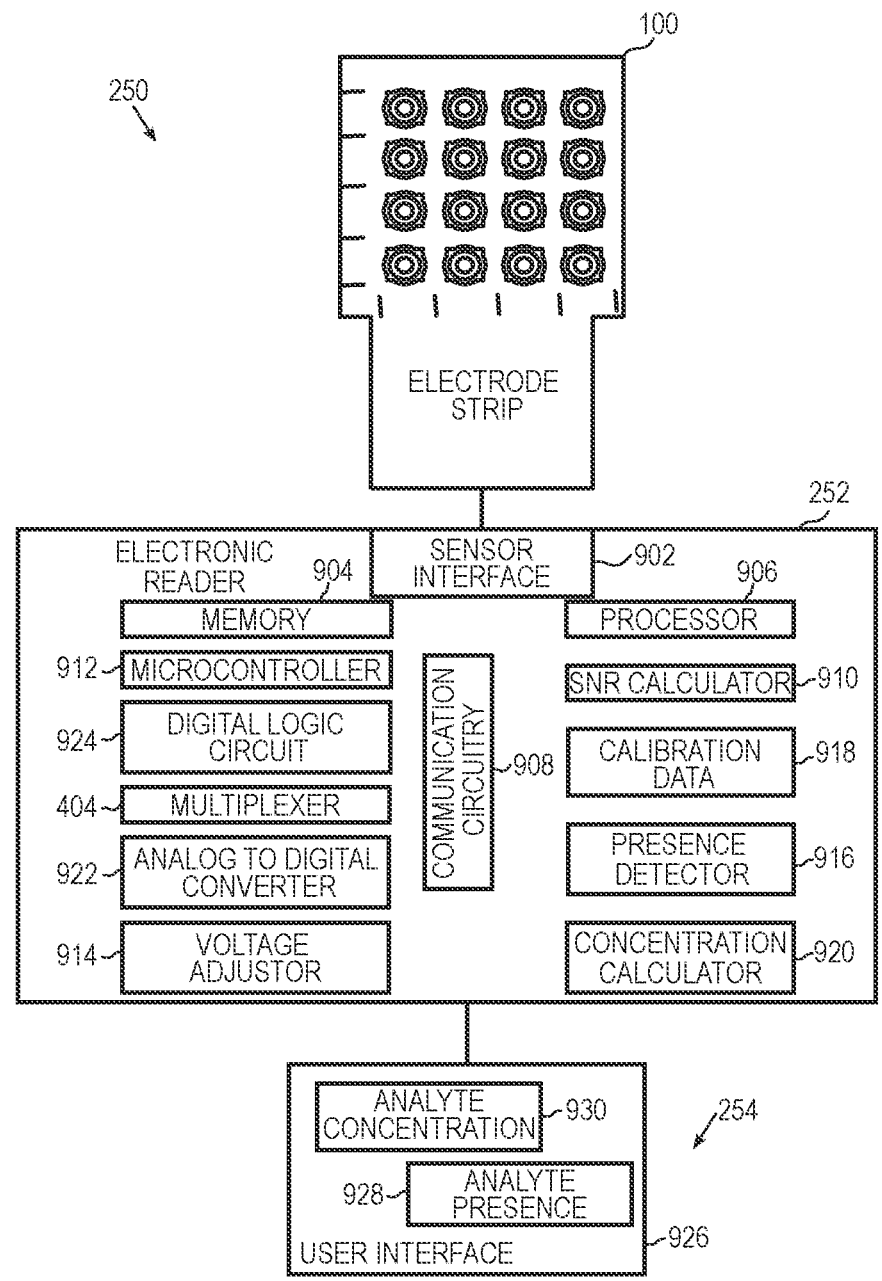
FIG. 9 is a simplified block diagram illustrating example details of a system for multi-modal and multiplexed electrochemical detection and reporting of environmental contaminants, according to some embodiments of the present disclosure.

FIG. 9 is a simplified block diagram illustrating example details of system 250 for multi-modal and multiplexed electrochemical detection and reporting of environmental contaminants, according to some embodiments of the present disclosure. Electrode strip 100 may be physically and conductively coupled during testing to electronic reader 252 through sensor interface 902. In various embodiments, contact pads 112 conductively coupled to sensors 114 may be in direct conductive contact with mating contact pads in sensor interface 902 of electronic reader 252. In embodiments wherein electrode strip 100 is removably connected to electronic reader 252, sensor interface 902 may comprise any suitable board-to-board connector such as edge card connector.

Electronic reader 252 further comprises a memory 904 and a processor 906. Memory 904 may include one or more volatile memory devices such as dynamic random access memory (DRAM), nonvolatile memory (e.g., read-only memory (ROM)), flash memory, solid-state memory, and/or a hard drive. In some embodiments, memory 904 may include memory that shares a die with processor 906. Memory 904 may include algorithms, code, software modules, and applications, which may be executed by processor 906. As used herein, the term "processor" may refer to any device or portion of a device that processes electronic data from registers and/or memory to transform that electronic data into other electronic data that may be stored in registers and/or memory. Processor 906 may include one or more digital signal processors (DSPs), Application Specific Integrated Circuits (ASICs), CPUs, GPUs, server processors, or any other suitable processing devices.

Electronic reader 252 may include communication circuitry 908 for interfacing with electrode strip 100, and external computing devices 256 (not shown). For example, communication circuitry 908 may be configured for managing wireless communications for the transfer of data to and from electronic reader 252. The term "wireless" and its derivatives may be used to describe circuits, devices, systems, methods, techniques, communications channels, etc., that may communicate data through modulated electromagnetic radiation in a nonsolid medium. The term does not imply that the associated devices do not contain any wires, although in some embodiments they might not.

Communication circuitry 908 may implement any of a number of wireless standards or protocols, including but not limited to Institute for Electrical and Electronic Engineers (IEEE) standards including Wi-Fi(IEEE 802.11 family), IEEE 802.16 standards (e.g., IEEE 802.16-2005 Amendment), Long Term Evolution (LTE) project along with any amendments, updates, and/or revisions (e.g., advanced LTE project, ultramobile broadband (UMB) project (also referred to as "3GPP2"), etc.). Communication circuitry 908 may operate in accordance with a Global System for Mobile Communication (GSM), General Packet Radio Service (GPRS), Universal Mobile Telecommunications System (UMTS), High-Speed Packet Access (HSPA), Evolved HSPA (E-HSPA), or LTE network. Communication circuitry 908 may operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). Communication circuitry 908 may operate in accordance with Code Division Multiple Access (CDMA), Time Division Multiple Access (TDMA), Digital Enhanced Cordless Telecommunications (DECT), Evolution-Data Optimized (EV-DO), and derivatives thereof, as well as any other wireless protocols that are designated as 3G, 4G, 5G, and beyond. Communication circuitry 908 may operate in accordance with other wireless protocols in other embodiments. Communication circuitry 908 may include antennas to facilitate wireless communications and/or to receive other wireless communications.

In some embodiments, communication circuitry 908 may manage wired communications, such as electrical, optical, or any other suitable communication protocols (e.g., the Ethernet, Internet). Communication circuitry 908 may include multiple communication chips. For instance, a first communication chip may be dedicated to shorter-range wireless communications such as Wi-Fi or Bluetooth, and a second communication chip may be dedicated to longer-range wireless communications such as global positioning system (GPS), EDGE, GPRS, CDMA, WiMAX, LTE, EV-DO, or others. In some embodiments, a first communication chip may be dedicated to wireless communications, and a second communication chip may be dedicated to wired communications.

A signal to noise ratio (SNR) calculator 910 in electronic reader 252 may calculate a signal to noise ratio of electrical signals from electrode strip 100. A microcontroller 912 may generate voltage adjustments to a voltage adjustor 914 (e.g., potentiometer, rheostat, etc.), for example, to vary the SNR. In some embodiments, voltage adjustment may be continued until a maximum SNR is achieved. A presence detector 916 may compare the electrical signals from electrode strip 100 to stored calibration data 918 to determine whether or not analytes 134 are detected in sample 120. Calibration data 918 may correspond to known output ranges for known analyte concentrations as described in reference to FIG. 2B. A concentration calculator 920 may compare the electrical signals from electrode strip 100 to stored calibration data 918 to estimate concentration of analytes 134 in sample 120. In various embodiments, stored calibration data 918 can comprise calibration data from past tests under controlled conditions.

An analog-to-digital converter 922 in electronic reader 252 may digitize electrical signals from electrode strip 100 and feed the digital signals to digital logic circuit 924. Digital logic circuit 924 may transform the digital signals to an output that is fed to multiplexer 404. Multiplexer 404 may generate suitable output signals that may be sent to a user interface 926. User interface 926 may be provided by application 254 of computing device 256. Suitable displays 928 and 930 showing analyte presence and analyte concentration respectively may be provisioned in user display 926.

In many embodiments, memory 904 may store data, such as algorithms, software code, instructions, etc. for performing the measurement protocols as described herein. Processor 906 may cooperate with memory 904 for executing the various instructions stored thereon. In many embodiments, a user (e.g., lab technician) may introduce sample 120 into cartridge 104 through fluid inlet 106. The user may thereafter initiate a measurement protocol suitably, for example, through application 254 executing in computing device 256. Application 254 may call the instructions, algorithms, code, etc. stored in memory 904 and initiate the measurement protocol suitably. In some embodiments, the instructions may include waiting for an incubation period to pass before initiating electrical measurements, for example, to allow analytes 134 in sample 120 to bind with capture probes 132.

An instruction may be performed to cause voltage to be applied at electrodes 122 of sensors 114 in a particular channel (e.g., 500, 600, 700, 800, etc.) according to the multiplexing scheme being used for testing. In various embodiments, the voltage may be applied across each pair of first electrode 122a and second electrode 122b. In some embodiments, the voltage may be applied across all sensors 114 simultaneously even though measurements are being recorded only on one channel. In some embodiments, the instructions may include adjusting the voltage according to analytes 134 under test. The instructions may include measuring any response across electrodes 122 suitably and analyzing as described previously. In various embodiments, processor 906 may include specific circuit elements for executing such instructions stored in memory 904, for example, triggering or calling appropriate instruments (e.g., potentiometer, current source, etc.) as needed according to the corresponding instructions until the user stops the measurement protocols or the instructions reach a natural end of process.

Figure 10:
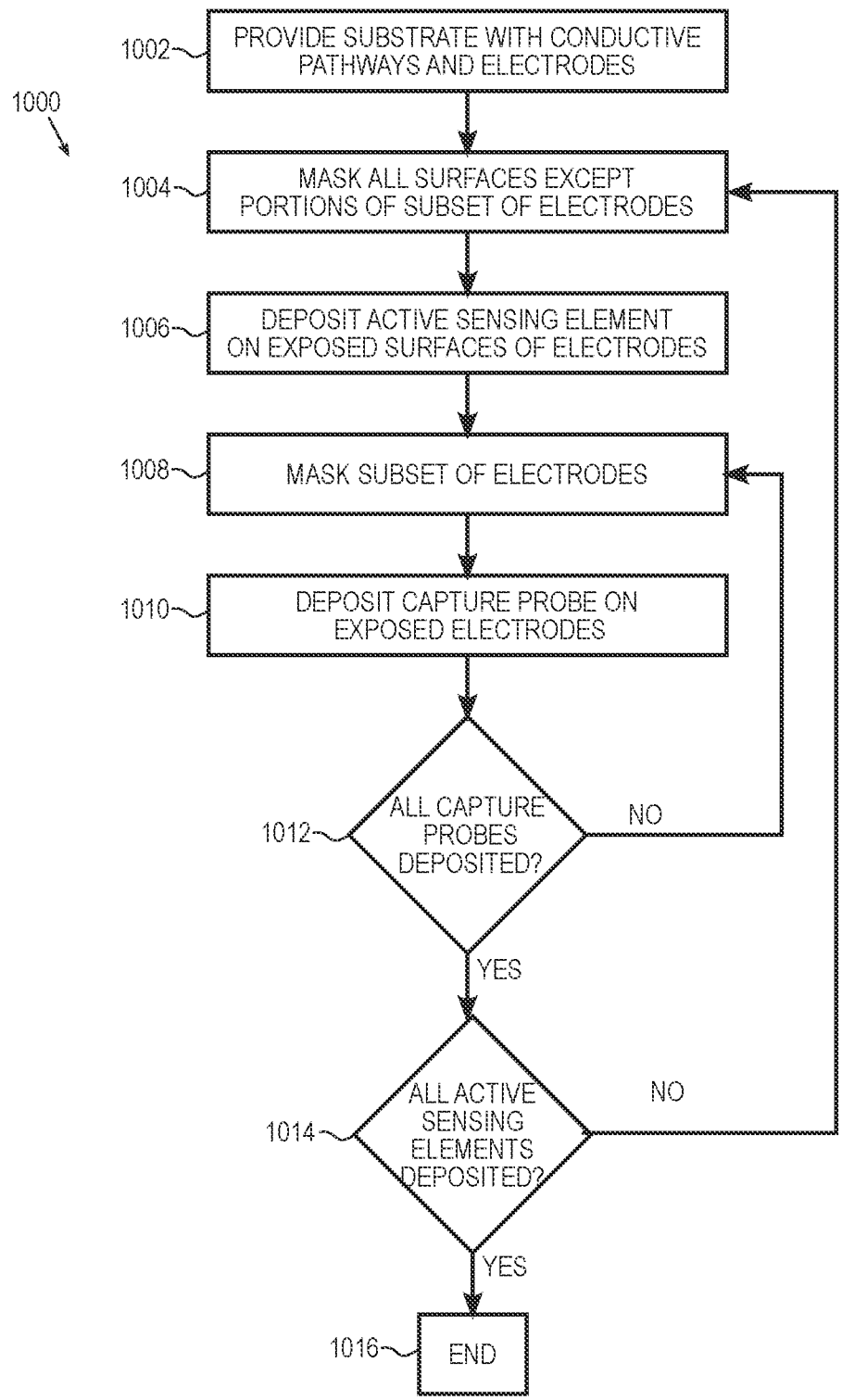
FIG. 10 is a simplified flow diagram illustrating example operations associated with a system for multi-modal and multiplexed electrochemical detection and reporting of environmental contaminants, according to some embodiments of the present disclosure.

FIG. 10 is a simplified flow diagram illustrating example operations 1000 associated with manufacturing electrode strip 100 in system 250, according to some embodiments of the present disclosure. At 1002, substrate 102 may be provided with conductive pathways 116 and electrodes 122. In various embodiments, conductive pathways 116 and electrodes 122 may be fabricated using conventional PCB manufacturing processes, such as electrodeposition, etching, masking, etc. At 1004, all surfaces except portions of electrodes 122 may be masked. In some embodiments, only surfaces of a subset of first electrodes 122a may be exposed. In some embodiments, the subset may comprise all of first electrodes 122a in electrode strip 100.

The choice of the specific ones of first electrodes 122a to expose may depend on the test purposes of strip 100 and/or multiplexing configuration as described in the foregoing figures. For example, electrode strip 100 may be produced to test for 16 different analytes, including 134a of plastic pollutants 304 and analytes 134b of biological contaminants 306. Analytes 134a may be tested with a certain type of active sensing element 128a and analytes 134b may be tested with another type of active sensing element 128b. Sensors 114 may also be suitably divided according to the modulation schemes as described in FIGS. 5A-8B to generate subsets of first electrodes 122a.

Assume, merely for the sake of explanation, and not as a limitation, that the modulation scheme described in FIGS. 5A and 5B is used. Assume also, as an example and not as a limitation, that sensors 502A-502H are used to test for analytes 134a requiring active sensing element 128a and sensors 5021-502P are used to test for analytes 134b requiring active sensing element 128b. Thus, first electrodes 122a may be subdivided, for purposes of operation 1004, into a first subset corresponding to active sensing element 128a and a second subset corresponding to active sensing element 128b. The first subset of first electrodes 122a may be exposed and all remaining portions of substrate 102 may be masked.

At 1006, active sensing element 128 may be deposited on exposed surfaces of electrodes 122. Turning back to the example described with reference to operation 1004, active sensing element 128a may be deposited on the first subset of first electrodes 122a at 1006.

At 1008, another subset of electrodes 122 may be masked for application of capture probes 132 at 1010. At 1012 a determination may be made whether all capture probes 132 for the deposited active sensing element 128 have been deposited. If not, the operations may revert to 1008, and subsequent steps repeated until all capture probes 132 have been deposited. Turning back to the example described with reference to operation 1004, each one of sensors 502A-502H may be used to test for different ones of analytes 304a. Thus, each one of corresponding first electrodes 122a may be masked at 1008 and appropriate capture probes 132 deposited on the exposed first electrode 122a in turn until all appropriate capture probes 132 have been deposited.

After all capture probes 132 have been deposited at 1012, the operations may step to 1014. At 1014, a determination may be made whether all active sensing elements 128 have been deposited. If not, the operations may revert to 1004 and subsequent steps repeated until all active sensing elements 128 are deposited. Turning back to the example described with reference to operation 1004, the second subset of first electrodes 122a may be exposed at operation 1004 for deposition of active sensing element 128b. Subsequent steps may be repeated until all capture probes 132 have been deposited on active sensing element 128b.

After all active sensing elements 128 and capture probes 132 have been deposited on first electrodes 122a in electrode strip 100 as desired and based on particular needs, the operations may end at 1016.

FIG. 11 is a simplified flow diagram illustrating example operations 1100 associated with system 250, according to some embodiments of the present disclosure. At 1102, sample 120 may be introduced into enclosed space 118 in cartridge 104, for example, by pipetting sample 120 through fluid inlet 106. At 1104, testing may be paused for a suitable incubation period to allow analytes 134 in sample 120 to bind with capture probes 132. At 1106, a voltage may be applied at electrodes 122 of one or more sensors 114 in a particular channel according to the multiplexing scheme being used for testing. In various embodiments, the voltage may be applied across each pair of first electrode 122a and second electrode 122b. In some embodiments, the voltage may be applied across all sensors 114 simultaneously even though measurements are being recorded only on one channel.

At 1108, the voltage may be adjusted according to analytes 134. For example, some analytes 134a may be detected at a first voltage and some other analytes 134b may be detected at a different second voltage. A previous measurement protocol for analyte 134a may have used a particular voltage value, and such voltage value may be changed for the measurement protocol being performed to detect analyte 134b.

At 1110, response across electrodes 122 may be measured suitably. For example, electrical signals from electrodes 122 may be captured by electronic reader 252 over sensor interface 902. At 1112, the response may be compared to stored calibration data 918. At 1114, based on the comparison, the presence of analytes 134 may be detected. At 1116, based on the comparison, the concentration of analytes 134 may be estimated. At 1118, the presence and concentration values may be transmitted to user interface 926. At 1120, a determination may be made whether all channels have completed testing. If not, the operations revert to 1106 and subsequent operations are repeated for the next channel; and so on until all channels are completed. The operations may end at 1122.

Although FIGS. 10 and 11 illustrate various operations performed in a particular order, this is simply illustrative, and the operations discussed herein may be reordered and/or repeated as suitable. Further, additional operations which are not illustrated may also be performed without departing from the scope of the present disclosure. Also, various ones of the operations discussed herein with respect to FIGS. 10-11 may be modified in accordance with the present disclosure suitably based on particular needs. For example, with reference to FIG. 11, in some embodiments, operation 1118 may be performed after all channels have completed testing, so that a collective response may be presented on user interface 926. In other embodiments, operation 1118 may be performed for each channel separately. Although various operations are illustrated in FIGS. 10-11 once each, the operations may be repeated as often as desired, for example, to make multiple electrode strips 100 and perform tests using multiple electrode strips 100 suitably based on particular needs.

Select Examples

Example 1 provides an apparatus (e.g., 100), comprising a substrate (e.g., 102) having a first end and an opposite, second end; a plurality of sensors (e.g., 114) proximate to the first end of the substrate, each sensor including a first electrode (e.g., 122); a second electrode (e.g., 122b) at least partially surrounding the first electrode; and an active sensing element (e.g., 128) over the first electrode, a surface (e.g., 130) of the active sensing element being functionalized to detect analytes (e.g., 134) in a sample (e.g., 120) derived from an environmental source (e.g., 200); a plurality of contact pads (e.g., 112) proximate to the second end of the substrate, each contact pad being conductively coupled to the first electrode or the second electrode of a corresponding sensor in the plurality of sensors; and a cartridge (e.g., 104) surrounding the plurality of sensors and providing an enclosed space (e.g., 118) to contain the sample over the plurality of sensors.

Example 2 provides the apparatus of example 1, in which the environmental source is a liquid, and the sample comprises a portion of the liquid.

Example 3 provides the apparatus of example 1, in which the environmental source is a solid, and the sample comprises at least one of: (i) puree of the solid mixed with at least one of water and a saline solution, (ii) supernatant of a suspension including crushed pieces of the solid mixed with at least one of water and a saline solution, and (iii) runoff from the solid washed in at least one of water and a saline solution.

Example 4 provides the apparatus of any one of examples 1-3, in which the environmental source comprises at least one of: food (e.g., 202), water (e.g., 204), soil (e.g., 206), plastics (e.g., 208), and cosmetics (e.g., 210).

Example 5 provides the apparatus of example 4, in which the food comprises raw, cooked, or processed vegetables, fruits, dairy products, fish, or meat.

Example 6 provides the apparatus of example 4, in which the food comprises vitamins or mineral supplements.

Example 7 provides the apparatus of any one of examples 1-6, in which the analytes are derived from at least one of: plastic pollutants (e.g., 304), biological contaminants (e.g., 306), chemical/synthetic agents (e.g., 308), and food allergens (e.g., 310).

Example 8 provides the apparatus of example 7, in which the plastic pollutants comprise at least one of: (i) per- and polyfluoroalkyl substances (PFAS), (ii) bisphenols, (iii) phthalates, and (iv) polychlorinated biphenyls.

Example 9 provides the apparatus of example 7, in which the biological contaminants include at least one of: (i) pathogens and (ii) mycotoxins.

Example 10 provides the apparatus of example 7, in which the chemical/synthetic agents include at least one of: (i) pesticides and (ii) genetically modified organisms (GMO) based food.

Example 11 provides the apparatus of example 7, in which the food allergens comprise at least one: milk, eggs, fish, crustacean shellfish, tree nuts, peanuts, wheat, soybeans, and sesame.

Example 12 provides the apparatus of any one of examples 1-11, in which the cartridge comprises a fluid inlet and a plurality of vent holes, and the sample is introduced into the enclosed space through the fluid inlet.

Example 13 provides the apparatus of any one of examples 1-12, in which the first electrode and the second electrode are approximately circular in shape, the second electrode is concentric with the first electrode.

Example 14 provides the apparatus of any one of examples 1-13, in which the substrate comprises a first layer (e.g., 126a) and a different, second layer (e.g., 126b), the first electrode and the second electrode are in the first layer of the substrate, the first electrode is conductively coupled by a conductive pathway (e.g., 116a) in the second layer of the substrate to a first contact pad in the plurality of contact pads, the first contact pad is in the second layer of the substrate, the second electrode is conductively coupled by another conductive pathway (e.g., 116b) in the first layer of the substrate to a second contact pad (e.g., 122b) in the plurality of contact pads, and the second contact pad is in the first layer of the substrate.

Example 15 provides the apparatus of any one of examples 1-14, in which the plurality of sensors comprises discrete subsets, and the active sensing element in any one subset bind to different analytes compared to the active sensing element in other subsets.

Example 16 provides the apparatus of example 15, in which the plurality of sensors comprises sixteen sensors, and each subset comprises a single sensor.

Example 17 provides the apparatus of example 15, in which the plurality of sensors comprises sixteen sensors, and each subset comprises two sensors.

Example 18 provides the apparatus of example 15, in which the plurality of sensors comprises sixteen sensors, and each subset comprises four sensors.

Example 19 provides the apparatus of example 15, in which the plurality of sensors comprises sixteen sensors, and each subset comprises eight sensors.

Example 20 provides the apparatus of any one of examples 1-19, in which the active sensing element comprises at least one of: a semiconductor thin-film and a room temperature ionic liquid (RTIL) thin-film.

Example 21 provides a system, comprising an electrode strip, including a plurality of sensors at one end and contact pads at an opposing other end, each sensor in the plurality of sensors comprising a first electrode and a second electrode configured to detect analytes in a sample derived from environmental sources; and a cartridge covering the plurality of sensors, the cartridge providing an enclosed space over the plurality of sensors for enclosing the sample; an electronic reader comprising a sensor interface configured to conductively and physically couple with the contact pads of the electrode strip; a memory configured to store data; a processor; a microcontroller; a voltage adjustor; and a communication circuitry, in which the processor executes instructions associated with the data, the processor is coupled to the communication circuitry and the memory, and the processor and the memory cooperate, such that the system is configured for applying a voltage across the first electrode and the second electrode of one or more sensors in the plurality of sensors, the voltage being controlled by the microcontroller; measuring a response to the voltage; comparing the response to stored calibration data; and responsive to the comparison, determining at least one of: (i) a presence of an analyte and (ii) a concentration of the analyte in the sample.

Example 22 provides the system of example 21, further comprising a user interface, in which at least one of: the presence of the analyte or the concentration of the analyte is displayed on the user interface.

Example 23 provides the system of example 22, in which the user interface is in a computing device separate from the electronic reader.

Example 24 provides the system of example 22, in which the electronic reader interfaces with the user interface using the communication circuitry over at least one of a wired connection and a wireless connection.

Example 25 provides the system of any one of examples 21-25, in which the plurality of sensors is configured to detect a plurality of analytes according to a multiplexing scheme, the plurality of sensors is categorized into different subsets, and one or more sensors in each subset is configured to detect a different analyte compared to sensors in other subsets.

Example 26 provides a method, comprising providing an electrode strip comprising a plurality of sensors at one end and contact pads at an opposing other end, each sensor in the plurality of sensors comprising a first electrode and a second electrode configured to detect analytes in a sample derived from environmental sources; and a cartridge covering the plurality of sensors, the cartridge including a fluid inlet and providing an enclosed space over the plurality of sensors for enclosing the sample; introducing the sample into the enclosed space through the fluid inlet; applying a voltage across the first electrode and the second electrode of one or more sensors in the plurality of sensors; measuring a response to the voltage; comparing the response to stored calibration data; and responsive to the comparison, determining at least one of: (i) a presence of an analyte and (ii) a concentration of the analyte in the sample.

Example 27 provides the method of example 26, further comprising a user interface, in which at least one of: the presence of the analyte or the concentration of the analyte is displayed on the user interface.

Example 28 provides the method of any one of examples 26-27, in which the plurality of sensors is configured to detect a plurality of analytes according to a multiplexing scheme.

Example 29 provides the method of example 28, in which the plurality of sensors is categorized into different subsets, and one or more sensors in each subset is configured to detect a different analyte compared to sensors in other subsets.

Example 30 provides the method of example 29, in which applying the voltage, measuring the response, comparing the response and determining are repeated for each subset separately.

The above description of illustrated implementations of the disclosure, including what is described in the abstract, is not intended to be exhaustive or to limit the disclosure to the precise forms disclosed. While specific implementations of, and examples for, the disclosure are described herein for illustrative purposes, various equivalent modifications are possible within the scope of the disclosure, as those skilled in the relevant art will recognize

The invention claimed is:

1. An apparatus, comprising:
a substrate having a first end and an opposite, second end;
a plurality of sensors proximate to the first end of the substrate, each sensor including:
    a first electrode;
    a second electrode at least partially surrounding the first electrode; and
    an active sensing element over the first electrode, a surface of the active sensing element being functionalized to detect analytes in a sample derived from an environmental source;
a plurality of contact pads proximate to the second end of the substrate, each contact pad being conductively coupled to the first electrode or the second electrode of a corresponding sensor in the plurality of sensors;
a cartridge surrounding the plurality of sensors and providing an enclosed space to contain the sample over the plurality of sensors; and
a sensing circuitry coupled to the plurality of contact pads, the sensing circuitry configured to analyze electrical impedance and capacitance signals by concurrently analyzing a set of Nyquist plots obtained via a modified electrochemical impedance spectroscopy (EIS) technique and a set of Mott-Schottky plots obtained via a Mott-Schottky technique, wherein the modified EIS technique comprises sectioning an interfacial charge layer into a plurality of spatial dielectric planes along a direction orthogonal to an interface between the sample and the active sensing element and probing each of the plurality of spatial dielectric planes with a specific frequency selected from a range of frequencies.

2. The apparatus of claim 1, wherein:
the environmental source is a liquid, and
the sample comprises a portion of the liquid.

3. The apparatus of claim 1, wherein:
the environmental source is a solid, and
the sample comprises at least one of: (i) puree of the solid mixed with at least one of water and a saline solution, (ii) supernatant of a suspension including crushed pieces of the solid mixed with at least one of water and a saline solution, and (iii) runoff from the solid washed in at least one of water and a saline solution.

4. The apparatus of claim 1, wherein the environmental source comprises at least one of: food, water, soil, plastics, and cosmetics.

5. The apparatus of claim 1, wherein the analytes are derived from at least one of: plastic pollutants, biological contaminants, chemical agents, and food allergens.

6. The apparatus of claim 5, wherein the plastic pollutants comprise at least one of: (i) per- and polyfluoroalkyl substances (PFAS), (ii) bisphenols, (iii) phthalates, and (iv) polychlorinated biphenyls.

7. The apparatus of claim 5, wherein the biological contaminants include at least one of: (i) pathogens and (ii) mycotoxins.

8. The apparatus of claim 5, wherein the chemical agents include at least one of: (i) pesticides and (ii) genetically modified organisms (GMO) based food.

9. The apparatus of claim 5, wherein the food allergens comprise at least one: milk, eggs, fish, crustacean shellfish, tree nuts, peanuts, wheat, soybeans, and sesame.

10. The apparatus of claim 1, wherein:
the cartridge comprises a fluid inlet and a plurality of vent holes, and
the sample is introduced into the enclosed space through the fluid inlet.

11. The apparatus of claim 1, wherein:
the plurality of sensors comprises discrete subsets, and
the active sensing element in any one subset detects a different analyte compared to the active sensing element in other subsets.

12. A system, comprising:
an electrode strip, including:
a plurality of sensors at one end and contact pads at an opposing other end, each sensor in the plurality of sensors comprising a first electrode and a second electrode configured to detect analytes in a sample derived from environmental sources; and
a cartridge covering the plurality of sensors, the cartridge providing an enclosed space over the plurality of sensors for enclosing the sample;
an electronic reader comprising:
a sensor interface configured to conductively and physically couple with the contact pads of the electrode strip;
a memory configured to store data;
a processor;
a microcontroller;
a voltage adjustor;
a sensing circuitry comprising a signal-to-noise ratio (SNR) calculator, a presence detector, a concentration calculator, an analog to digital converter, a digital logic circuit, and a multiplexer, the sensing circuitry configured to analyze electrical impedance and capacitance signals by concurrently analyzing a set of Nyquist plots obtained via a modified electrochemical impedance spectroscopy (EIS) technique and a set of Mott-Schottky plots obtained via a Mott-Schottky technique, wherein the modified EIS technique comprises sectioning an interfacial charge layer into a plurality of spatial dielectric planes along a direction orthogonal to an interface between the sample and the sensors and probing each of the plurality of spatial dielectric planes with a specific frequency selected from a range of frequencies; and
a communication circuitry, wherein the processor executes instructions associated with the data, the processor is coupled to the communication circuitry and the memory, and the processor and the memory cooperate, such that the system is configured for:
applying a voltage across the first electrode and the second electrode of one or more sensors in the plurality of sensors, the voltage being controlled by the microcontroller;
measuring a response to the voltage, the response comprising the electrical impedance and capacitance signals;
comparing the response to stored calibration data; and
responsive to comparing the response, determining at least one of: (i) a presence of an analyte and (ii) a concentration of the analyte in the sample.

13. The system of claim 12, further comprising a user interface, wherein at least one of: the presence of the analyte or the concentration of the analyte is displayed on the user interface.

14. The system of claim 13, wherein the electronic reader interfaces with the user interface using the communication circuitry over at least one of a wired connection and a wireless connection.

15. The system of claim 12, wherein:
the plurality of sensors is configured to detect a plurality of analytes according to a multiplexing scheme,
the plurality of sensors is categorized into different subsets, and
one or more sensors in each subset is configured to detect a different analyte compared to sensors in other subsets.

16. A method, comprising:
providing an electrode strip comprising:
a plurality of sensors at one end and contact pads at an opposing other end, each sensor in the plurality of sensors comprising a first electrode and a second electrode configured to detect analytes in a sample derived from environmental sources; and
a cartridge covering the plurality of sensors, the cartridge including a fluid inlet and providing an enclosed space over the plurality of sensors for enclosing the sample;
introducing the sample into the enclosed space through the fluid inlet;
applying a voltage across the first electrode and the second electrode of one or more sensors in the plurality of sensors;
measuring a response to the voltage, the response comprising electrical impedance and capacitance signals;
analyzing the electrical impedance and capacitance signals by concurrently analyzing a set of Nyquist plots obtained via a modified electrochemical impedance spectroscopy (EIS) technique and a set of Mott-Schottky plots obtained via a Mott-Schottky technique, wherein the modified EIS technique comprises sectioning an interfacial charge layer into a plurality of spatial dielectric planes along a direction orthogonal to an interface between the sample and the sensors and probing each of the plurality of spatial dielectric planes with a specific frequency selected from a range of frequencies;
comparing the analyzed response to stored calibration data; and
responsive to comparing the analyzed response, determining at least one of: (i) a presence of an analyte and (ii) a concentration of the analyte in the sample.

17. The method of claim 16, further comprising a user interface, wherein at least one of: the presence of the analyte or the concentration of the analyte is displayed on the user interface.

18. The method of claim 16, wherein the plurality of sensors is configured to detect a plurality of analytes according to a multiplexing scheme.

19. The method of claim 18, wherein:
the plurality of sensors is categorized into different subsets, and
one or more sensors in each subset is configured to detect a different analyte compared to sensors in other subsets.

20. The method of claim 19, wherein applying the voltage, measuring the response, comparing the response and determining are repeated for each subset separately.

* * * * *